(12) United States Patent
Constantz et al.

(10) Patent No.: US 6,562,020 B1
(45) Date of Patent: *May 13, 2003

(54) KITS FOR USE IN THE TREATMENT OF VASCULAR CALCIFIED LESIONS

(75) Inventors: Brent R. Constantz, Menlo Park, CA (US); Peter Johansson, Menlo Park, CA (US)

(73) Assignee: Corazon Technologies, Inc., Menlo Park, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/483,634

(22) Filed: Jan. 14, 2000

Related U.S. Application Data

(63) Continuation-in-part of application No. 09/425,826, filed on Oct. 22, 1999, now Pat. No. 6,290,689, and a continuation-in-part of application No. 09/384,860, filed on Aug. 27, 1999, and a continuation-in-part of application No. 09/353,127, filed on Jul. 14, 1999, now Pat. No. 6,379,345, which is a continuation-in-part of application No. 09/195,291, filed on Nov. 18, 1998, now Pat. No. 6,387,071, which is a continuation-in-part of application No. 09/118,193, filed on Jul. 15, 1998, now Pat. No. 6,394,096.

(51) Int. Cl.[7] .............................................. A61M 25/00
(52) U.S. Cl. ........................ 604/523; 604/43; 604/171; 604/27
(58) Field of Search .............................. 604/523, 93.01, 604/27, 43, 48, 264, 171

(56) References Cited

U.S. PATENT DOCUMENTS

| | | | |
|---|---|---|---|
| 4,445,892 A | 5/1984 | Hussein et al. | |
| 4,573,966 A | 3/1986 | Weikl et al. | |
| 4,610,662 A | 9/1986 | Weikl et al. | |
| 4,636,195 A | 1/1987 | Wolinsky | |
| 4,655,746 A | 4/1987 | Daniels et al. | |
| 4,824,436 A | 4/1989 | Wolinsky | |
| 4,883,459 A | * 11/1989 | Calderon | 600/4 |
| 4,911,163 A | 3/1990 | Fina | |
| 4,976,733 A | 12/1990 | Girardot | |
| 5,059,178 A | 10/1991 | Ya | |
| 5,090,960 A | 2/1992 | Don Michael | |
| 5,135,484 A | * 8/1992 | Wright | 604/101.03 |
| 5,167,628 A | 12/1992 | Boyles | |
| 5,195,955 A | 3/1993 | Don Michael | |
| 5,222,941 A | 6/1993 | Don Michael | |
| 5,380,284 A | 1/1995 | Don Michael | |
| 5,443,446 A | 8/1995 | Shturman | |
| 5,462,529 A | 10/1995 | Simpson | |
| 6,044,845 A | * 4/2000 | Lewis | 128/898 |
| 6,295,990 B1 | * 10/2001 | Lewis et al. | 128/898 |

* cited by examiner

*Primary Examiner*—Brian L. Casler
*Assistant Examiner*—Jeremy Thissell
(74) *Attorney, Agent, or Firm*—Bret E. Field; Bozicevic, Field & Francis

(57) ABSTRACT

Kits for use in the treatment of vascular calcified lesions are provided. The subject kits include at least one of: (a) a fluid delivery means for conveying fluid to and from a vascular site; and (b) a dissolution fluid for at least partially dissolving the target lesion. In many embodiments, the kits include both of these components. The subject kits further include instructions for treating vascular calcified lesions with the contents of the kit, where the instructions are typically recorded on a recording medium, e.g. printed on a substrate, such as paper.

23 Claims, 16 Drawing Sheets

Section A-A
Not to scale

Total Occlusion Catheter

Partial Occlusion Catheter (w/ Balloon)

Section A-A
Not to scale

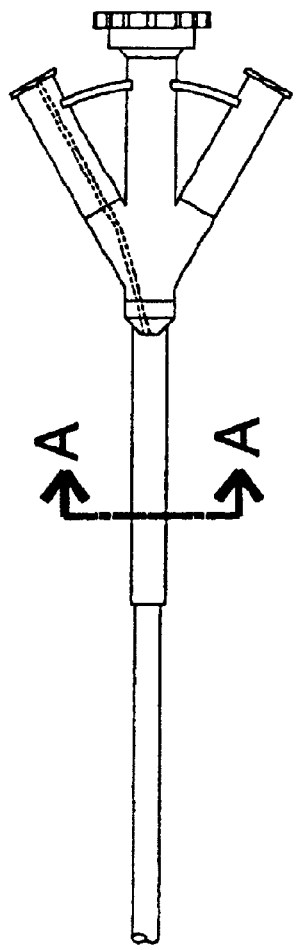
FIG. 13
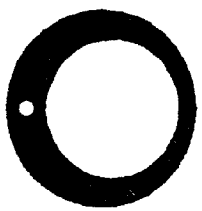
Section A-A
Not to scale
Irrigation Catheter

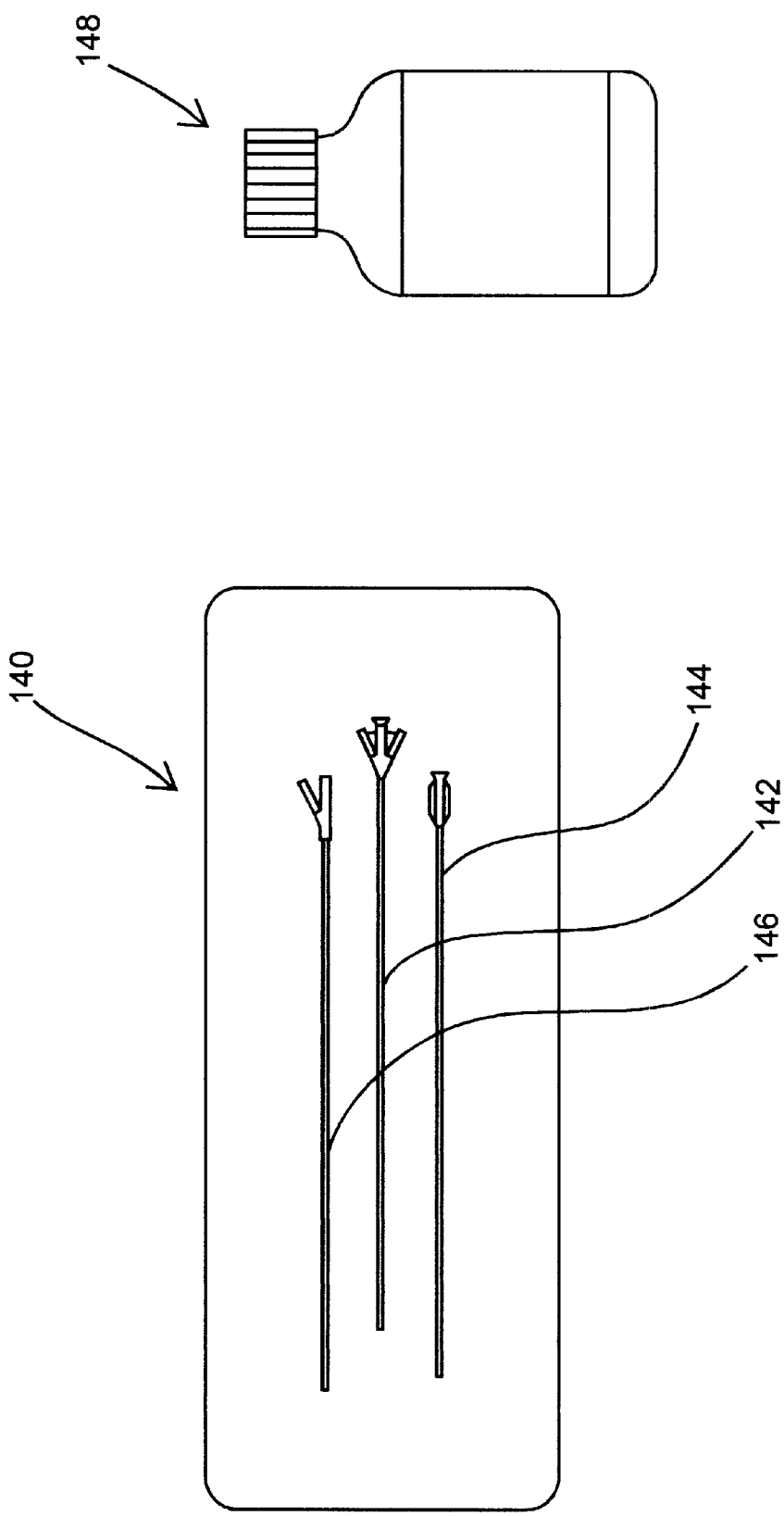

KITS FOR USE IN THE TREATMENT OF VASCULAR CALCIFIED LESIONS

CROSS-REFERENCE TO RELATED APPLICATIONS

This application is a continuation-in-part of: (a) application Ser. No. 09/425,826 filed Oct. 22, 1999 now U.S. Pat. No. 6,290,689; (b) application Ser. No. 09/384,860 filed Aug. 27, 1999; and (c) application Ser. No. 09/353,127, filed Jul. 14, 1999 now U.S. Pat. No. 6,379,345; which application is, in turn, a continuation-in-part of application Ser. No. 09/195,291 filed Nov. 18, 1998 now U.S. Pat. No. 6,387,071 which application is a continuation-in-part of application Ser. No. 09/118,193 filed Jul. 15, 1998 now U.S. Pat. No. 6,394,096; the disclosures of which applications are herein incorporated by reference.

INTRODUCTION

1. Field of the Invention

The field of this invention is atherosclerosis and related vascular-conditions.

2. Background of the Invention

The formation of plaques or lesions, (atherosclerotic plaques or lesions) on cardiovascular tissue, such as the inner surface of blood vessels, aortic valves, etc., is a major component of cardiovascular disease. Many atherosclerotic plaques and lesions are characterized by the presence of mineral deposits, i.e. they are calcified. Calcified lesion formation on prosthetic devices is also a problem in current cardiovascular disease treatment protocols. For example, calcification is an important limitation on the useful life expectancy of bioprosthetic valves, and accounts for over sixty percent of the cardiac bioprostheses failures.

A variety of different protocols have been developed for treating cardiovascular diseases associated with the presence of calcified lesions. Such treatment methodologies generally involve mechanical removal or reduction of the lesion, and include: bypass surgery, balloon angioplasty, mechanical debridement, atherectomy, valve replacement, and the like. Despite the plethora of different treatment strategies that have been developed for the treatment of cardiovascular disease, there are disadvantages associated with each technique, such as tissue damage, invasiveness, etc. For example, restenosis is a common complication that results in arteries in which lesions have been mechanically removed.

As such, there is continued interest in the development of new treatment protocols for the removal of vascular calcified lesions from vascular tissue, as well as kits of components that are used in such protocols.

Relevant Literature

U.S. Patents of interest include: U.S. Pat. Nos. 4,445,892; 4,573,966; 4,610,662; 4,636,195; 4,655,746; 4,824,436; 4,911,163; 4,976,733; 5,059,178; 5,090,960; 5,167,628; 5,222,941; 5,380,284; 5,443,446; and 5,462,529.

SUMMARY OF THE INVENTION

Kits for use in the treatment of vascular calcified lesions are provided. The subject kits include at least one of: (a) a fluid delivery means for conveying fluid to and from a vascular site; and (b) a dissolution fluid for at least partially dissolving the target lesion. In many embodiments, the kits include both of these components. The subject kits further include instructions for treating vascular calcified lesions with the contents of the kit, where the instructions are typically recorded on a recording medium, e.g. printed on a substrate, such as paper.

BRIEF DESCRIPTION OF THE FIGURES

FIG. 13 provides another view of an aspiration or irrigation catheter of the catheter systems that may be found in kits of the subject invention.

FIG. 14 provides a view of a kit according to the subject invention, where the kit includes the components of a catheter system which can be assembled into partial and total occlusion configurations and a container of dissolution fluid.

DESCRIPTION OF THE SPECIFIC EMBODIMENTS

Figure 1:
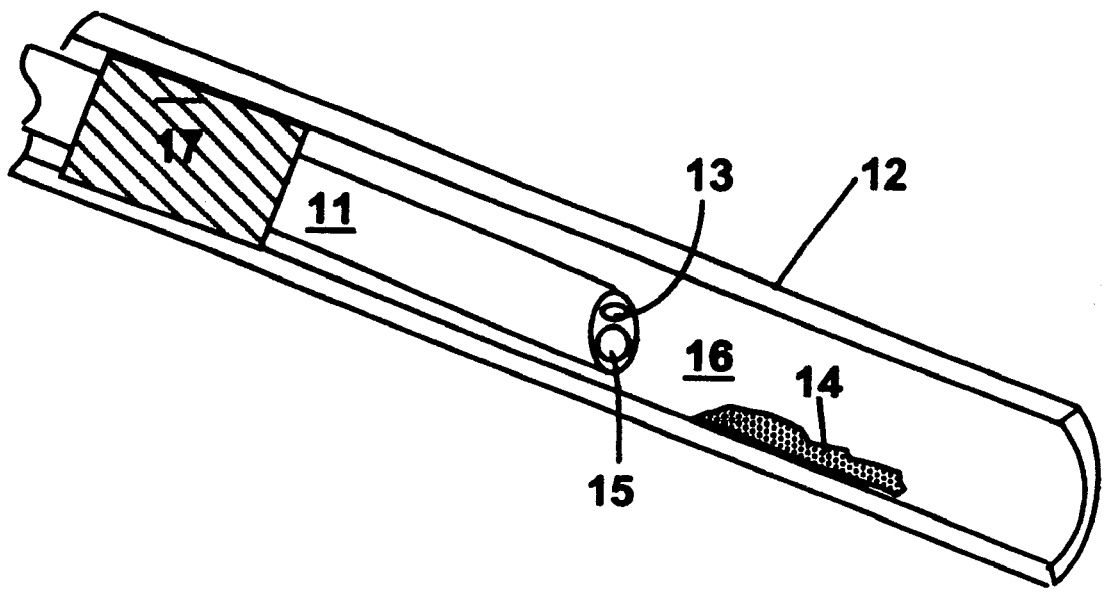
FIG. 1 provides a view of a first embodiment of a catheter fluid delivery means that may be present in a kit according to the subject invention.

Kits for use in the treatment of vascular calcified lesions are provided. The subject kits include at least one of: (a) a fluid delivery means for conveying fluid to and from a vascular site, e.g. for flushing a site with fluid; and (b) a dissolution fluid for at least partially dissolving the target lesion. In many embodiments, the kits include both of these components. The subject kits further include instructions for treating vascular calcified lesions with the contents of the kit, where the instructions are typically recorded on a recording medium, e.g. printed on a substrate, such as paper.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

It must be noted that as used in this specification and the appended claims, the singular forms "a," "an," and "the" include plural reference unless the context clearly dictates otherwise. Unless defined otherwise all technical and scientific terms used herein have the same meaning as commonly understood to one of ordinary skill in the art to which this invention belongs.

Overview of Kits

As summarized above, the present invention provides kits for use in treating vascular calcified lesions. The subject kits include at least one of: (a) a dissolution fluid (or one or more components thereof) and (b) a fluid delivery means, where in certain embodiments the kits may include both a dissolution fluid and a fluid delivery means. In addition, the kits include instructions for treating a vascular calcified lesion using a fluid delivery means and a dissolution fluid, where these instructions are recorded on a suitable recording medium, e.g. they are printed on a substrate such as paper. In addition to these required components, the kits may also include one or more optional components, e.g. pH elevating fluid, guidewire, etc. The required and optional components are now separately described in greater detail, below.

Dissolution Fluid

A variety of different types of dissolution fluids may be present in the kits of the subject invention, as long as the fluids are capable of increasing the proton concentration in a vascular site to a desired subphysiologic level sufficient to at least partially dissolve the mineral component of a mineral comprising lesion in a target vascular site. In other words, any fluid that is capable of providing the requisite subphysiologic pH in the local environment of the vascular site is suitable for use in the subject methods. In many embodiments, the dissolution fluid is a dissolution solution.

One type of solution that is of particular interest is an acidic dissolution or treatment solution. A variety of different types of acidic dissolution solutions may be present in the subject kits. The acidic treatment solutions that are present in the subject kits generally have a pH of less than about 6.5, where the pH is usually less than about 4.0 and more usually less than about 3.0. In many preferred embodiments, the pH ranges from 0 to 2, and usually 0 to 1. The acidic treatment solution can include a number of different types of acids, where the acids may or may not include a hydrocarbon moiety, i.e. a hydrogen bonded directly to a carbon atom. Suitable acids that lack a hydrocarbon moiety include halogen acids, oxy acids and mixtures thereof, where specific acids of interest of this type include, but are not limited to, hydrochloric, nitric, sulfuric, phosphoric, hydroboric, hydrobromic, carbonic and hydroiotic acids. For such acids, the acid can be a concentrated acid, or can be diluted. Upon dilution, the concentration of an inorganic acid will generally be from about 10 N to about 0.01 N, preferably between 5 N to 0.1 N. Also of interest are acids that include a hydrocarbon moiety, where such acids include, but are not limited to, any organic acid of one to six ($C_1$ to $C_6$) carbons in length. Organic acids of this type include, but are not limited to, formic, acetic, propionic, maleic, butanoic, valeric, hexanoic phenolic, cyclopentanecarboxylic, benzoic, and the like. For an organic acid, the acid can be in concentrated form, or can be diluted. The acidic treatment solution can be composed of either a monobasic or a polybasic acid. Acids are "monobasic" when they have only one replaceable hydrogen atom and yield only one series of salts (e.g., HCl). Acids are "polybasic" when they contain two or more hydrogen atoms which may be neutralized by alkalies and replaced by organic radicals.

In many embodiments of the subject invention, the acid solution is hypertonic by which is meant that the osomolarity of the solution is greater than that of whole blood, i.e. the osmolarity is greater than 300 mosmol. The solution may be rendered hypertonic by including any convenient component or components in the solution which provide for the desired elevated osmolarity.

Any convenient agent that is capable of increasing the osmolarity of the solution may be employed, where suitable agents include salts, sugars, and the like. In many embodiments, the agent that is employed to render the solution hypertonic is one or more, usually no more than three, and more usually no more than two, different salts. Generally, the salt concentration in these embodiments of the solution is at least about 100 mosmol, usually at least about 200 mosmol and more usually at least about 300 mosmol, where the concentration may be as high as 3000 mosmol or higher, depending on the particular salt being employed to render the solution hypertonic, where the solution may be saturated with respect to the salt in certain embodiments. Salts that may be present in the subject solutions include: NaCl, $MgCl_2$, Ringers, etc. where NaCl is preferred in many embodiments.

Of particular interest in many embodiments is a hydrogen chloride solution. In hydrogen chloride solutions of interest in these embodiments, the concentration of HCl in the solution ranges from about 0.001 to. 1.0 N, usually from about 0.01 to 1.0 N and more usually from about 0.1 to 1.0 N. In many, embodiments, the hydrogen chloride solution further includes one or more salts which make the solution hypertonic, as described above. In certain preferred embodiments, the salt is NaCl, where the concentration of NaCl in the solution is at least 0.05 M, usually at least 0.10 M, and more usually at least 0.15 M, where the concentration may be as high as 0.25 M or higher. In certain embodiments, the solution will be saturated with NaCl.

Of particular interest are aqueous hydrogen chloride solutions that consist of water, hydrogen chloride and NaCl. The concentration of hydrogen chloride in these solutions of particular interest ranges from about 0.01 to 1.0 N, usually from about 0.05 to 0.5 N and more usually from about 0.075 to 0.25 N. The concentration of NaCl in these solutions of particular interest ranges from about 0.05 to 0.25 M, usually from about 0.05 to 0.10 M.

The dissolution fluid may further include one or more pharmacologically active agents which modulate the tissue response at the vascular site. Such agents may include agents that promote healing, e.g. growth factors, antiinflammatory agents, e.g. statins, and other agents which serve to modulate the physiological response at the vascular site in a desired manner, or discourage healing, e.g. heparin.

Instead of including a dissolution fluid, the subject kits may include one or more components of the dissolution fluid which are combined to produce the dissolution fluid at a desired time. For example, the subject kits may include dried precursor components of the dissolution fluid which are combined with water to produce the dissolution fluid.

The dissolution fluid or component(s) thereof are present in the kit in a suitable container, e.g. a bottle, pouch, etc. which is capable of serving as a storage vessel for the this component of the kit and, preferably, capable of preserving the sterility of this component of the kit, as this component of the kit is preferably sterile, e.g. medical grade.

Fluid Delivery Means

The fluid introduction means of the subject kits may be any convenient means that is capable of introducing a dissolution fluid, e.g. acidic solution, into the target vascular site. In general, the fluid introduction means present in the subject kits should at least include a means for introducing dissolution fluid into the target vascular site. Typically, the means is a conduit, e.g. tube, which has an opening at its distal end (i.e. the end that comes closest to the lesion during use) and is in fluid communication at its proximal end with a source of, e.g. container holding, the dissolution fluid, where the fluid communication relationship can be established through direct contact of the lumen with the source or through one or more connecting means which establish the requisite fluid communication.

In many embodiments, the fluid introduction means also includes a fluid removal means for removing fluid from the target vascular site. Any convenient means may be employed for removing fluid, as well as debris, e.g. lesion particles, dissolved lesion components etc., from the local environment of the lesion. The fluid removal means may be incorporated into the fluid introduction means summarized above or be a separate component from the fluid introduction means. Thus, the fluid removal means may be a conduit or vessel which is a component of the fluid introduction means, or may be a conduit or vessel on a separate catheter, cannula etc, which is positioned "downstream" in the direction of blood flow from the site of introduction of the dissolution fluid.

In many embodiments, the fluid introduction means is a catheter. In many embodiments, catheters employed in the subject methods include at least one fluid introduction means for introducing a dissolution fluid to the vascular site and a fluid removal means for removing fluid from the vascular site of the lesion. In many embodiments, the catheter devices of the subject invention also typically include a means for isolating the target vascular site.

As mentioned above, the dissolution fluid introduction means is generally a lumen having a proximal end in fluid communication with the dissolution fluid source, e.g. a dissolution fluid reservoir, and an open distal end capable of being introduced into the target vascular site. By "lumen" is meant an elongated vessel having a tubular structure with a proximal and distal end, where the cross-sectional shape along the length of structure is generally (though not necessarily) circular, ovoid or some other curvilinear shape. The dissolution fluid introduction lumen has sufficient dimensions to allow for the desired flow rate at target vascular site. The exact dimensions for the fluid introduction lumen will vary depending, at least in part, on the nature of the dissolution fluid that is to be introduced in the region of the lesion. For example, with HCl solutions, fluid introduction lumens having inner diameters (ID) ranging from about 1 to 5 mm, usually from about 1 to 3 mm and more usually from about 1 to 2 mm are of interest. Alternatively, in those embodiments in which a pressurized dissolution fluid is delivered to the local environment of the lesion, e.g. where a carbonic acid solution is employed as the dissolution solution as described in U.S. patent application Ser. No. 09/353,127 (the disclosure of which is herein incorporated by reference), the dimensions are often sufficient to reduce bubble formation, e.g. $CO_2$ bubble formation. As such, the dissolution fluid introduction lumen has an inner diameter (ID) that is at least about 50 Fm, usually at least about 100 Fm and more usually at least about 200 Fm, where the inner diameter will typically not exceed about 2000 Fm and usually will not exceed about 1000 Fm. Depending on the configuration of the catheter device, the entire cross-sectional area may be available for fluid flow, or a portion of the cross-sectional area may be occupied by one or more additional device elements, e.g. a guide wire, one or more additional lumens, and the like, as described in greater detail infra. The fluid introduction lumen may be fabricated from a wide variety of materials. See the patents listed in the relevant literature section, supra. In those embodiments where the dissolution fluid is pressurized, as described above, the lumen is fabricated from materials capable of preserving the pressure of the fluid. Such materials are described in U.S. Pat. Nos. 5,599,296; 5,569,180; 5,693,017; 5,730,935; 5,735,934; and 5,797,874; the disclosures of which applications are herein incorporated by reference. Also of interest are multiple small lumens having ID of between about 50 and 80 Fm, usually around 75 Fm.

In addition to the fluid introduction means, the subject catheters typically further include a fluid removal means capable of removing fluid from the local region or environment of the lesion. A critical feature of the fluid removal means in many embodiments is that it is capable of removing fluid from the local environment of the lesion at the same rate as that at which fluid is introduced into the local environment of the lesion by the dissolution fluid introduction means. The fluid removal means is typically a lumen having dimensions that allow for adequate fluid flow from the local environment of the target lesion. In addition, in certain embodiments the dimensions of the second lumen are such that they allow passage of the debris from the local environment of the lesion through the second lumen. In such embodiments, the fluid removal lumen has an inner diameter that is substantially longer than the inner diameter of the fluid introduction lumen, where by substantially longer is meant at least about 2 fold longer, usually at least about 5 fold longer. As such, the fluid removal lumen typically has an inner diameter that is at least about 1 mm, usually at least about 2 mm and more usually at least about 3 mm, where the inner diameter typically does not exceed about 5 mm and usually does not exceed about 4 mm. The fluid removal lumen may be fabricated from any suitable material, where a variety of suitable materials are known to those of skill in the art.

In many embodiments, the subject device further includes a means for substantially isolating the vascular site from the remainder of the host's circulatory system so that the local environment can be rendered substantially, if not completely, bloodless. By substantially isolating is meant that fluid communication between the target vascular site and the remainder of the host's circulatory system is essentially removed—i.e. the target vascular site is no longer accessible by fluid from the remainder of the host's circulatory system or vice versa. Any convenient means may be employed for isolating the target vascular site. Such means include "cup" components that snugly fit over the target vascular site and thereby isolate it from the remainder of the circulatory system, dual balloon systems that inflate on either side of the lesion to isolate the local environment, etc.

In addition to the above components, the capillary devices of the subject invention, may further include: (a) one or more additional lumens, e.g. for introducing a rinse or wash fluid to the target vascular site; a means for allowing blood to flow through the isolated target vascular site, e.g. a pass through lumen; a means for applying energy to the target vascular site, e.g. an ultrasonic means; and visualization or monitoring means; etc.

All of the above components are conveniently present in a catheter device capable of accessing the vascular site of interest. The catheter device is capable of operatively communicating with other components and devices necessary for operation of the catheter, such as fluid flow means,.fluid reservoirs, power means, pressurized gas supply means, and the like, as described below, that are part of the overall system employed to practice the subject methods.

A number of catheter devices are known in the art that are capable of flushing an isolated vascular site with a solution, and these catheter devices may be present in the subject kits. Such catheter devices include those described in U.S. Pat. Nos. 4,573,966; 4,610,662; 4,636,195; 4,655,746; 4,824,436; 4,911,163; 5,059,178; 5,090,960; 5,163,905; 5,167,628; 5,176,638; 5,195,955; 5,222,941; 5,342,306; 5,380,284; 5,460,610; 5,833,644; 5,833,650; the disclosures of which are herein incorporated by reference.

Also of interest in many embodiments are the following novel representative catheter based fluid introduction means, which are also described in copending application Ser. No. 09/353,127, the disclosure of which is herein incorporated by reference. FIG. 1 provides a representation of first type of catheter device that may be present in the kits of the invention. Artery 12 (shown in cutaway view) has calcified lesion 14 on its inner surface 16. Catheter 11 is positioned proximal to the target lesion 14. At the distal end of catheter 11 is opening 13 which provides for flow of dissolution fluid from the catheter into the local environment of the lesion and opening 15 which provides for flow of fluid from the local environment of the lesion into the catheter and out of the patient. Catheter 11 also includes balloon element 17 which is inflated to render the local environment of the lesion, i.e. target vascular site, substantially bloodless.

Figure 2:
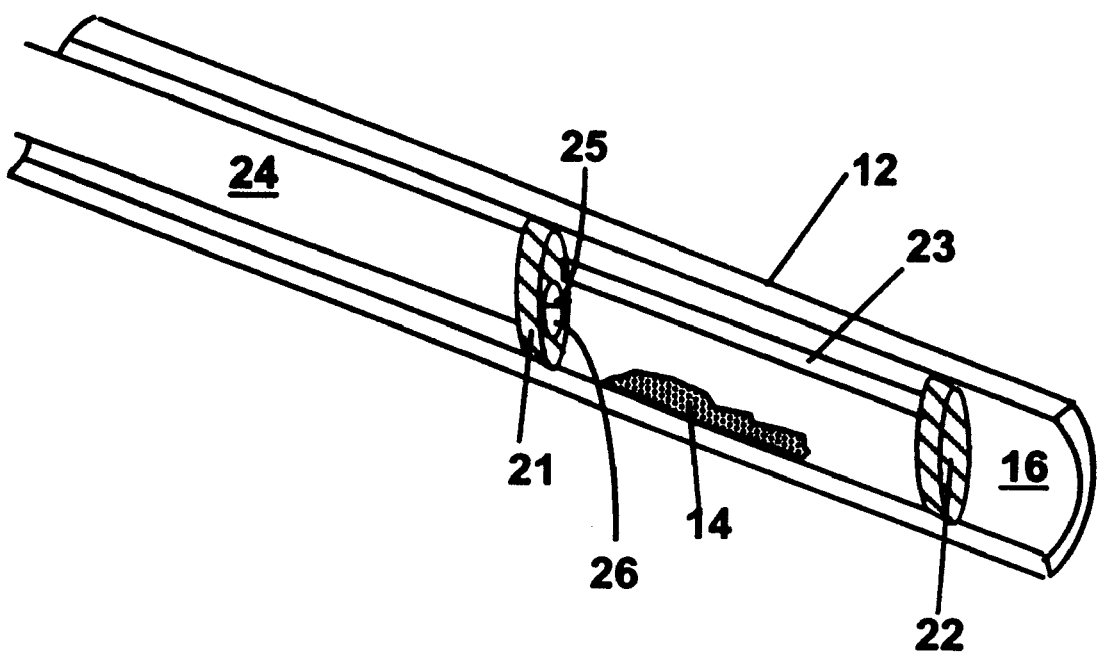
FIG. 2 provides a view of a second embodiment of a catheter fluid delivery means that may be present in a kit according to the subject invention.

FIG. 2 provides a representation of another catheter design that can be present in kits according to the subject invention. In FIG. 2, catheter 24 has two inflatable balloons 21 and 22 connected by a conduit 23 at its distal end. Catheter 24 also has fluid inflow opening 25 and fluid outflow opening 26 for introducing and removing dissolution fluid from the target vascular site. During use, the catheter is inserted and the balloons inflated such that the target vascular site becomes substantially sealed from the remainder of the host's circulatory system. The target vascular site is then flushed with dissolution fluid using openings 25 and 26.

Figure 3:
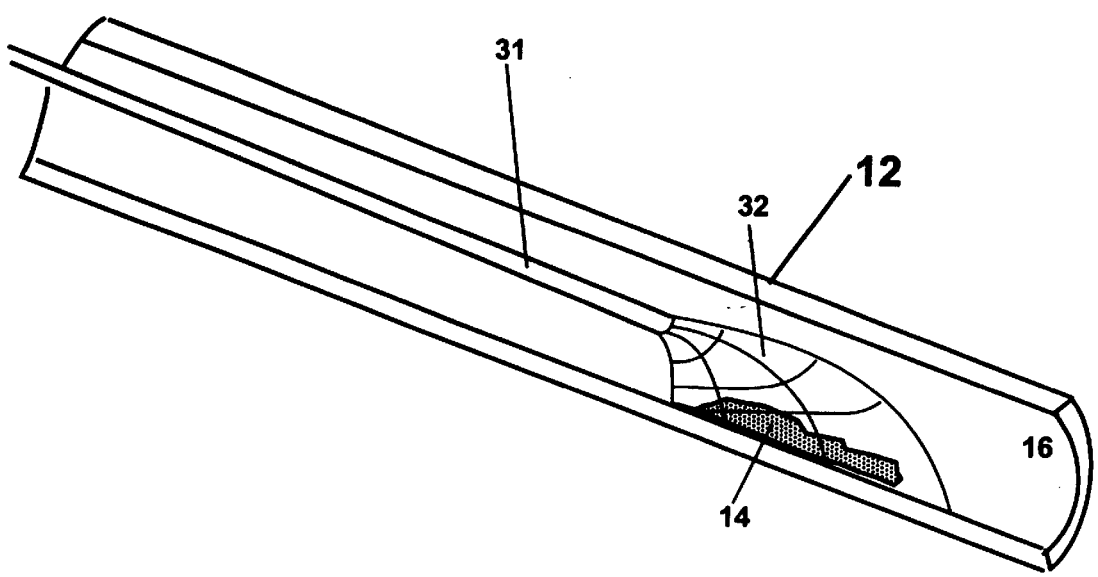
FIG. 3 provides a view of a third embodiment of a catheter fluid delivery means that may be present in a kit according to the subject invention.

FIG. 3 provides a representation of yet another catheter device that may be present in kits according to the subject invention. The catheter device is shown in artery 12 having calcified target lesion 14. Catheter 31 has a flexible cup 32 secured near the distal end of the catheter (shown in transparent lines). In one embodiment, the cup can be folded for insertion into the vessel, and then expanded at the desired location in the vicinity of the mineralized area. A defined area or local environment, i.e. target vascular site, is created by the contact of the cup 32 with the vessel wall 16. The catheter is designed to allow infusion of the local environment with the dissolution solution. The catheter is composed of flexible tubing such that it can be situated at any position along a vessel, and should be sufficiently strong so that it withstands the pressure created from the both the flow of the acidic treatment solution and the suction generated during the removal of the acidic treatment solution. Cup 32 can be held in place by maintaining the pressure within the local environment sufficiently below blood pressure, or optionally by a balloon (not shown) or other means. An ultrasound probe (not shown) may be used to generate ultrasonic energy.

In one embodiment, the catheter 31 is a single lumen catheter. The lumen of the catheter communicates with the interior of the flexible cup 32. A dissolution solution can be applied through the catheter to the local environment for the desired time period. Following this time period, the cup is removed, and the dissolution solution is allowed to disperse. Alternatively, a device to create suction can be applied to the more proximal end of the catheter so that the dissolution solution is drawn away from the defined area via the single lumen. Similarly, following treatment with the dissolution solution the rinsing agent can be applied through the single-lumen catheter, if desired.

In another embodiment, the catheter 31 is a double-lumen catheter, both of which communicate with the interior of the flexible cup 32. One of the lumens allows the infusion of either the dissolution solution or a rinsing solution. The second lumen removes the dissolution or rinse solution. Infusion and suction can be alternated, or the two processes can be applied simultaneously to create a flow of solution.

In yet another embodiment, catheter 31 is a triple-lumen catheter, all of which communicate with the interior of flexible cup 32. In this embodiment, one of the lumens allows the infusion of the dissolution solution, one of the lumens allows the infusion of a rinsing solution, and one of the lumens allow for the application of suction for the removal of solution.

Figure 4:
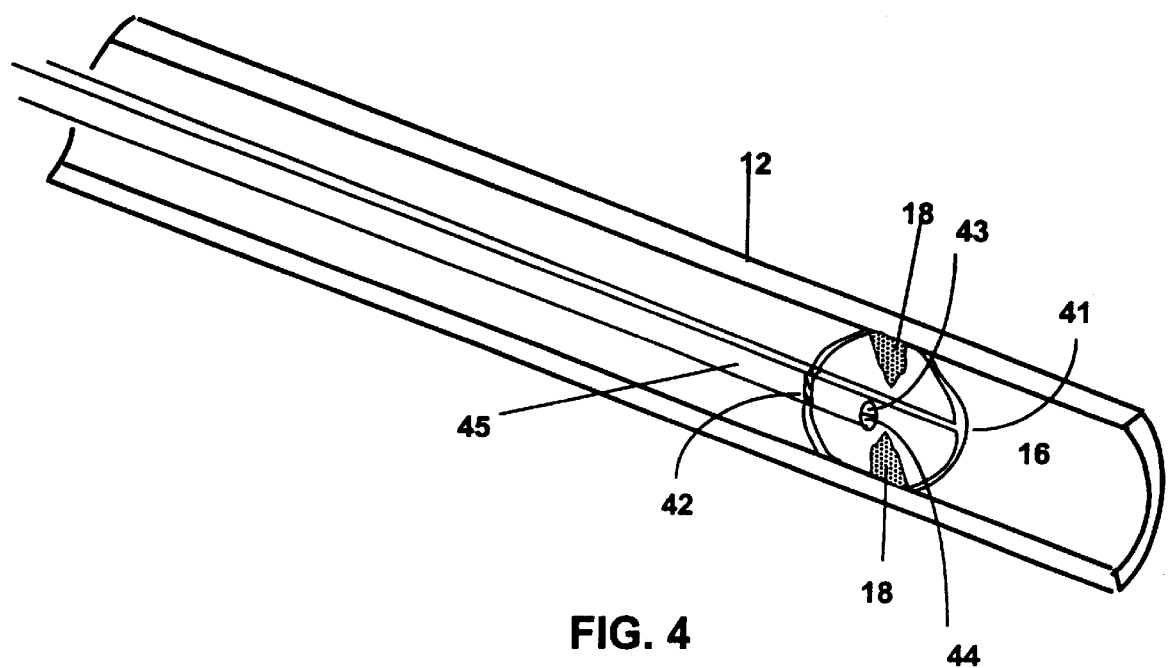
FIG. 4 provides a view of a fourth embodiment of a catheter fluid delivery means that may be present in a kit according to the subject invention.

Referring to FIG. 4, a double cup assembly device that may be present in the subject kits is shown. In this apparatus, catheter 45 includes first and second expandable cups 41 and 42. The cups can be placed on either side of a calcified target lesion, such as a calcified valve 18 shown in FIG. 4. This first cup 42 is placed in close proximity to one side of valve 18. One lumen of the catheter passes through the opening of the valve 18, as is terminates at second cup 41, which is placed in close proximity to the opposite side of the valve. Catheter 45 also includes fluid introduction 43 and fluid extraction 44 openings for introducing and removing fluid from the local environment bounded by the cups 41 and 42.

In certain embodiments, the fluid introduction means is a coaxial catheter device, as described in U.S. patent application Ser. No. 09/384,860, the disclosure of which is incorporated herein by reference. In these embodiments, the subject kits typically include a catheter system suitable for delivery of a fluid to a vascular site, and particularly for delivery of an acidic dissolution fluid to a surface of vascular occlusion. By catheter system is meant two more disparate catheter components which are capable of being assembled into a single unit, i.e. coaxial catheter assembly, having an inner catheter that is slidably positioned within the lumen of an outer catheter, i.e. a coaxial catheter assembly having an inner insert catheter that can be moved relative to the outer catheter so as to produce varying distances between the distal ends of the two coaxial catheters. One of the catheter components typically serves as the aspiration catheter and the other component as the acidic dissolution fluid introducing catheter.

The aspiration catheter is generally an elongated tubular structure fabricated from a flexible, biologically acceptable material having a balloon or analogous vessel occlusion means positioned at its distal end. The length of the aspiration catheter may vary, but is generally from about 80 to 200 cm, usually from about 90 to 180 cm and more usually from about 100 to 140 cm. The outer diameter of the aspiration catheter is selected so as to provide for access of the distal end of the catheter to the vascular site via the vascular system from the remote point of entry, where the outer diameter typically ranges from about 1.0 to 4.0 mm (3 to 12 Fr), usually from about 1.5 to 3.0 mm (4.5 to 9.0 Fr) and more usually from about 1.7 to 2.7 mm (5 to 8 Fr). The aspiration catheter is characterized by having an open distal end, where the inner diameter at the open distal end is sufficient to house either a partial or total occlusion insert catheter and remove fluid from the vascular site at the desired rate, e.g. a rate that provides for substantially isometric or isobaric pressure in the vascular site during treatment, through the resultant annular space. The aspiration catheter at least includes an aspiration lumen. The inner diameter of the aspiration lumen, at least at its distal end and generally along the entire length of the aspiration catheter, typically ranges from about 0.2 to 2.0, usually from about 0.25 to 1.75 and more usually from about 0.35 to 1.5 mm. Also present at the distal end of the aspiration catheter is a vessel occlusion means, where the vessel occlusion means is usually an inflatable balloon. The balloon is one that is inflatable to a volume sufficient to substantially occlude the vessel in which the aspiration catheter is positions, e.g. by pressing against the intimal surface of the vessel in which the aspiration catheter is positioned. The balloon is in fluid or gaseous communication with an inflation lumen that runs the length of the aspiration catheter and can be connected to a balloon inflation means. The inflation lumen has ail inner diameter that typically ranges from about 0.1 to 0.5, usually from about 0.2 to 0.4 mm. In certain embodiments, the aspiration catheter further includes a separate guidewire lumen. When present, the guidewire lumen has a diameter ranging from about 0.2 to 1.0 mm, usually from about 0.3 to 0.6 mm. Thus, the aspiration catheter includes at least two distinct lumens, i.e. an aspiration lumen and a balloon inflation lumen, and in many embodiments includes three distinct lumens, i.e. an aspiration lumen, a balloon inflation lumen and a guidewire lumen.

Figures 5A, 5B:
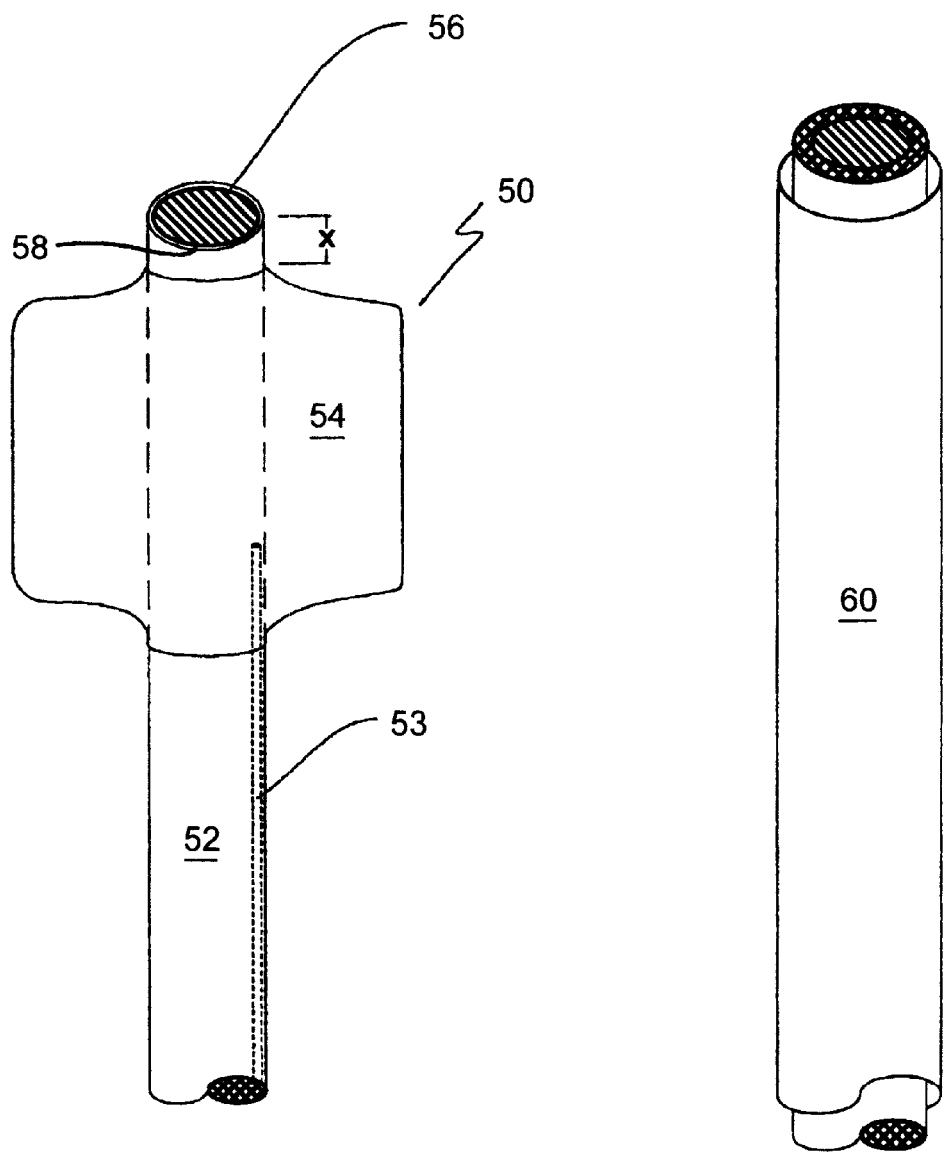
FIGS. 5A and 5B provide representations of an aspiration catheter and a total occlusion insert catheter, respectively, which are components of a catheter system that may be present in one embodiment of the subject kits, while FIG. 5C provides a representation of the total occlusion insert catheter inserted into the lumen of the aspiration catheter to form a coaxial catheter assembly.

A representation of the aspiration catheter of the subject catheter systems found in the subject kits is provided in FIG. 5A. In FIG. 5A, aspiration catheter 50.includes elongated tubular member 52 and balloon 54 located proximal to the distal end. The distance X between the distal most portion of the balloon 54 and the distal end of the catheter typically ranges from about 1 to 20, usually from about 5 to 10 mm. Also shown is distal open end 56 through which either the partial or total occlusion insert catheter is moved and fluid is aspirated. Balloon 54 is inflatable via balloon inflation lumen 53. Finally, device 50 is shown with optional guidewire lumen 58.

The aspiration catheter is further characterized by being capable of attaching, either directly or through one or more attachment means, at its proximal end to vacuum means, e.g. a negative pressure:means, where such means is sufficient to provide for the desired aspiration during use of the device, and a balloon inflation means, where such means is sufficient to inflate the balloon at the distal end of the catheter when desired.

In addition to the aspiration catheters, the catheter systems of this embodiment of the subject kits also include at least one catheter insert, where the catheter insert is capable of being slidably positioned within the lumen of the aspiration catheter and is either a total occlusion catheter insert or a partial occlusion catheter insert.

The total occlusion catheter insert is an elongated tubular structure having a blunt ended, open distal end through which fluid may be flowed under pressure. The length of the total occlusion catheter insert generally ranges from about 90 to 210 cm, usually from about 100 to 190 cm and more usually from about 110 to 150 cm. The outer diameter of the total occlusion catheter insert is such that the catheter insert may be slidably positioned in the lumen of the aspiration catheter, and typically ranges from about 0.5 to 2.0, usually from about 0.8 to 1.6 mm. The inner diameter of the total occlusion catheter insert typically ranges from about 0.2 to 1.0, usually from about 0.25 to 1.0 and more usually from about 0.3 to 1.0 mm. The total occlusion catheter insert (as well as the other catheter components of the subject catheter systems) generally has a circular cross-sectional shape, but the cross-sectional shape could be any convenient cross-sectional shape, including ovoid, irregular etc. A representation of a total occlusion catheter insert 60 according to the subject invention is provided in FIG. 5B.

Figure 5C:
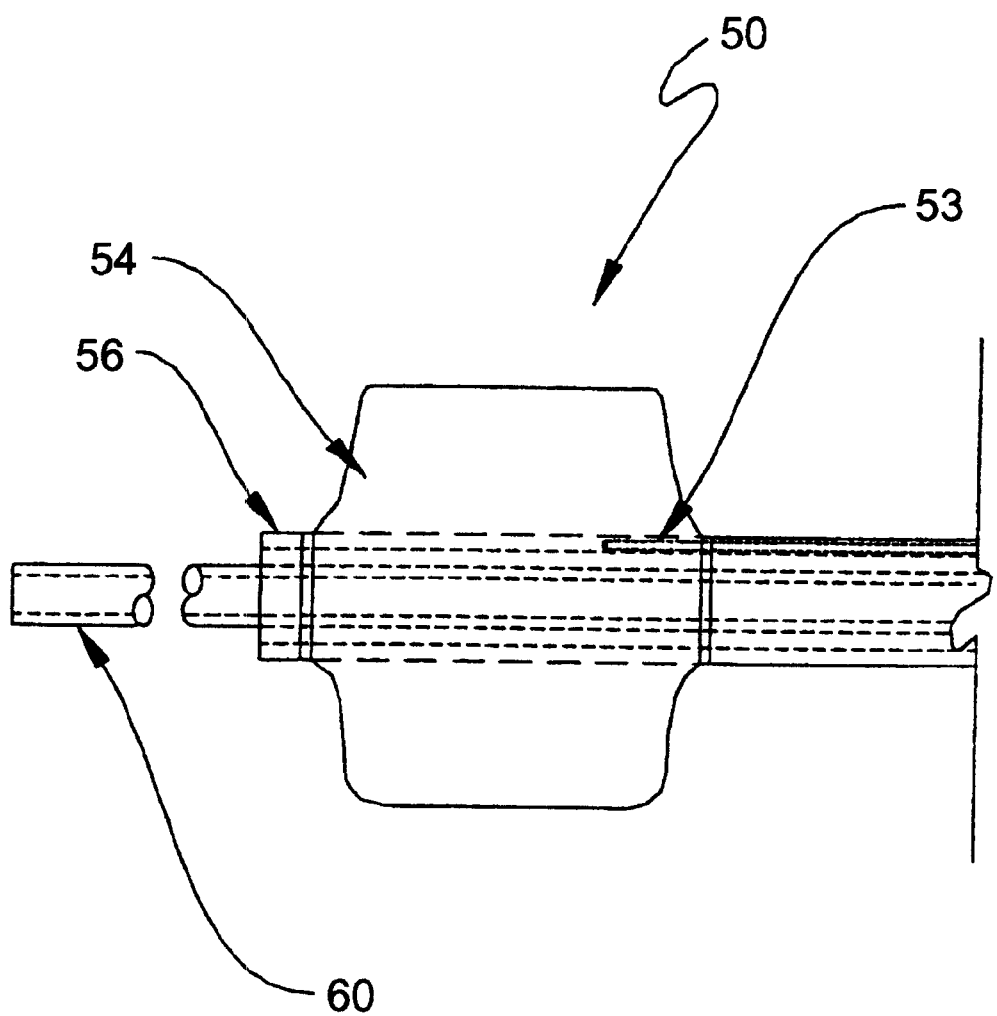

A representation of the total occlusion catheter insert positioned inside the lumen of an aspiration catheter (i.e. as a coaxial catheter assembly) and ready for use in the subject methods, as described infra, is provided in FIG. 5C. In the coaxial catheter assembly shown in FIG. 5C, the total occlusion catheter insert and the aspiration catheter are coaxial catheters. In FIG. 5C, total occlusion catheter insert 60 is slidably positioned in the lumen of aspiration catheter 50. Also shown is occlusion balloon 54 which is inflated and deflated through fluid/gaseous flow through balloon inflation lumen 53.

Alternatively or in addition to the total occlusion catheter insert described above, the subject catheter systems may also include a partial occlusion catheter insert. The partial occlusion catheter insert differs from the total occlusion catheter insert in a number of ways. First, the total occlusion vascular insert includes a balloon or analogous vessel occlusion means at its distal end. Second, the total occlusion vascular insert has one or more fluid introduction ports proximal to the proximal side of the distal balloon. Finally, the end of the partial occlusion catheter insert is sealed. The length of the partial occlusion catheter insert generally ranges from about 90 to 250 cm, usually from about 100 to 230 cm and more usually from about 110 to 190 cm . The outer diameter of the partial occlusion catheter insert is such that the catheter insert may be slidably positioned in the aspiration lumen of the aspiration catheter, and typically ranges from about 0.5 to 2.0, usually from about 0.8 to 1.6 mm. The inner diameter of the total occlusion catheter insert typically ranges from about 0.2 to 1.0, usually from about 0.25 to 1.0 and more usually from about 0.3 to 1.0 mm.

Figure 6A:
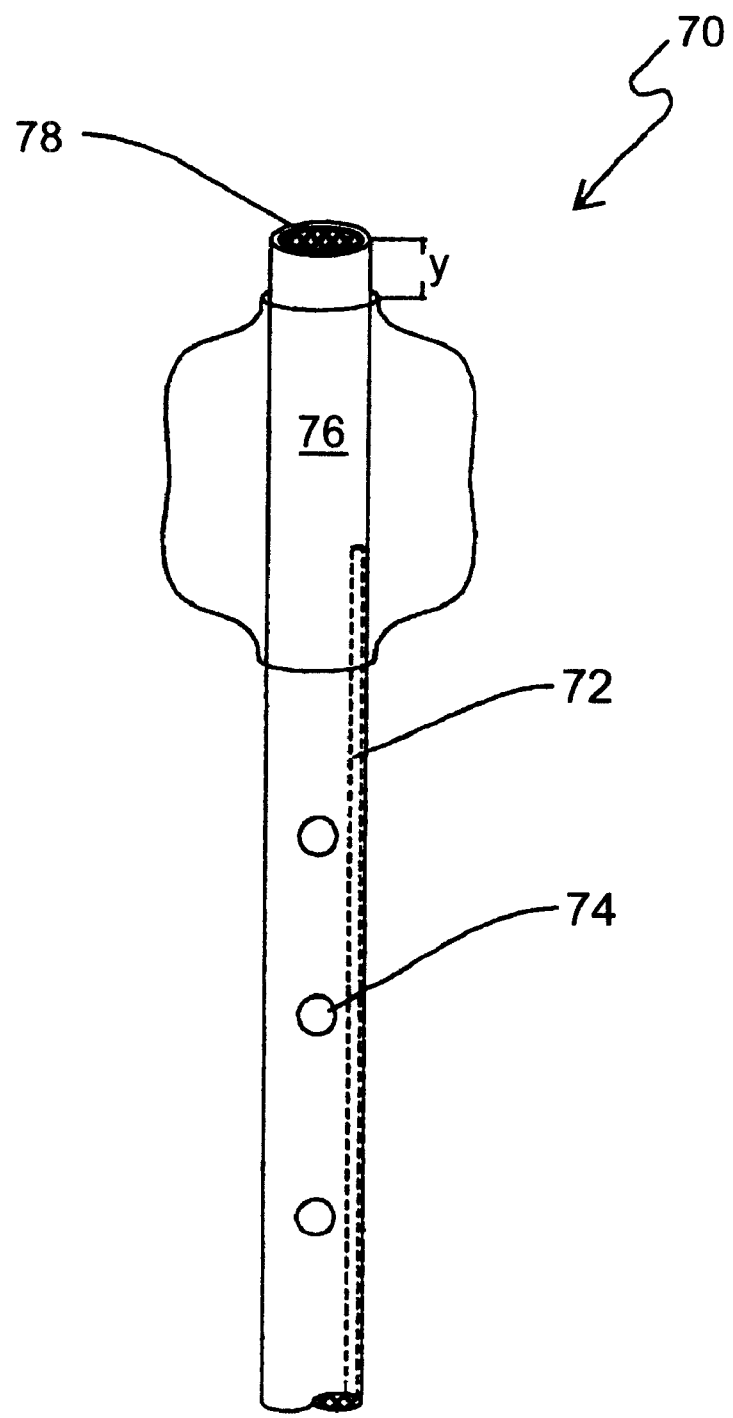
FIG. 6A provides a representation of a partial occlusion insert catheter while FIG. 6B provides a representation of the partial occlusion insert catheter inserted into the lumen of the aspiration catheter of FIG. 5A to form a coaxial catheter assembly.

A representative, partial occlusion catheter insert is provided in FIG. 6A. In FIG. 6A, partial occlusion catheter insert 70 includes elongated tubular structure 72 that is sealed at its distal end 78. Proximal to the distal end 78 is balloon 76, where the distance Y typically ranges from about 1 to 30 mm, usually from about 10 to 20 mm. Also depicted are infusion ports 74. The diameter of the infusion ports may vary, but typically ranges from about 0.2 to 1.2, usually from about 0.4 to 1.0 and more usually from about 0.5 to 0.8 mm. Not shown is the balloon inflation lumen, where the balloon inflation lumen has dimensions similar to those of balloon inflation lumen 53. As evidenced, the partial occlusion catheter insert includes two lumens, a fluid introduction lumen and a balloon inflation lumen.

Figure 6B:
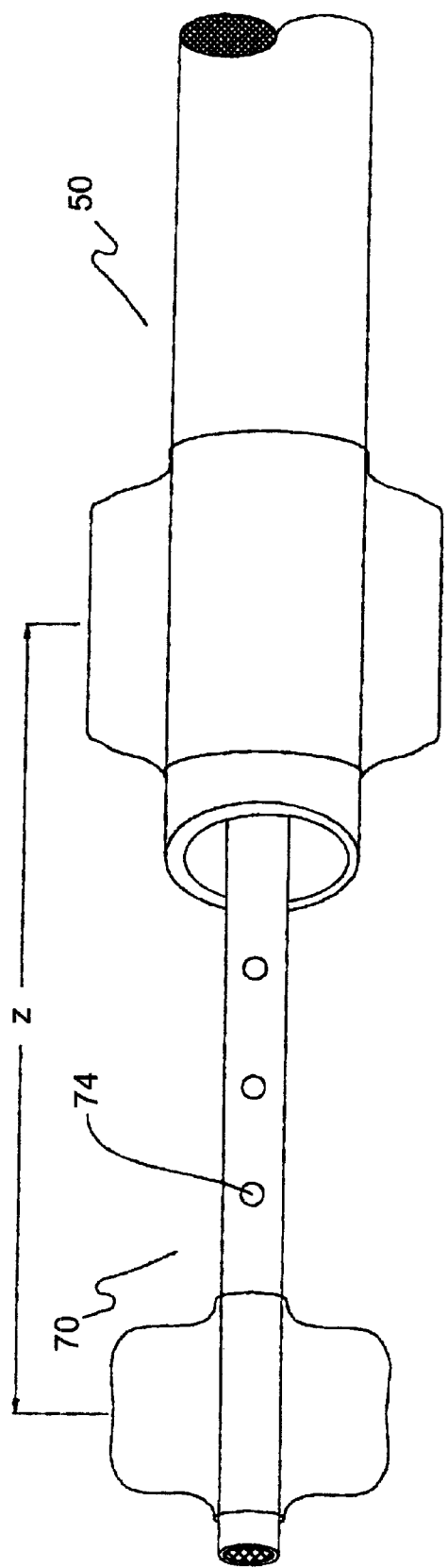

FIG. 6B shows the catheter assembly produced by insertion of the partial occlusion catheter into the aspiration catheter. In FIG. 6B, partial occlusion catheter 70 is slidably positioned in the lumen of aspiration catheter 50. positioned with respect to one another, the distance Z between the two balloons may vary, where during any given treatment procedure the distance Z may range from 1.5 to 45, usually from about 2 to 30 cm. Infusion ports 74 are provided for entry of a solution into the occluded space and fluid is then aspirated through the distal end of the aspiration catheter.

The catheter inserts are further characterized by being capable of being attached at their proximal ends, either directly or through one or more attachment means, to a fluid reservoir, e.g. an acidic dissolution fluid reservoir and, in the case of the partial occlusion catheter insert, a balloon inflation means.

While the above described catheter systems have been described in terms of an outer aspiration catheter and a catheter insert which serves to introduce fluid into a vascular site, i.e. as a fluid introduction means, during use of the subject systems (as described in greater detail below) these relative functions may be reversed, such that fluid is introduced through the outer, aspiration catheter and removed through the catheter insert.

In certain embodiments, the subject kits comprise a catheter or catheter system that is capable of simultaneously administering two distinct fluids, e.g. a dissolution fluid and a pH elevating fluid, to the target vascular site at the same time. Such catheters and catheter systems are described in U.S. patent application Ser. No. 09/425,826, the disclosure of which is herein incorporated by reference.

In such embodiments, the catheter devices which are found in, or can be made from components found in, the subject kits are multi-lumen catheter devices that comprise at least three distinct lumens, i.e. a first, second and third lumen.

The first lumen is characterized in that it has at least an inner wall that is resistant to reaction with an acidic dissolution fluid, at least for a period of time sufficient for the intended use of the catheter to be completed. More specifically, at least the inner wall of the catheter is fabricated from a material that is resistant to reaction with a solution having a pH of less than about 4, preferably less than about 2 and more preferably less than about 1. As such, it must be inert-to absolution that has a pH from about 0 to 4. Generally, the material from which the inner surface of the first lumen is fabricated must be resistant to reaction with an acidic solution, e.g. must be substantially inert with respect to the acidic dissolution fluid, for a period of time that is at least about 10 min long, preferably at least about 20 min long and more preferably for at least about 1 hour long or longer. Materials of interest from which at least the inner surface of the first lumen may be fabricated include: biocompatible polymers, e.g. polyimide, PBAX, polyethylene, and the like. The thickness of the inner surface of the first lumen must be sufficient to protect the remainder of the catheter device from any corrosive reaction with the acidic dissolution solution that is conveyed or delivered through the first lumen during use of the catheter device, as described in greater detail infra. As such, the thickness of the inner wall is typically at least about 0.5 mm, usually at least about 0.1 mm and more usually at least about 0.25 mm. The first lumen of the subject multi-lumen catheter devices is further characterized in that it is capable of being attached in fluid communication, either directly or indirectly, with an acidic dissolution fluid reservoir. The effective total cross sectional area through which acidic dissolution fluid flows during use of the subject devices, (i.e. the total cross-sectional areas of any openings present at the distal end of the first lumen less any area occupied by a blocking element positioned in any of the openings) is sufficient to provide the requisite rate of flushing of the vascular occlusion with the acidic dissolution fluid. Generally, the effective total cross sectional area provided by the at least one opening at the distal end of the first lumen is at least about 0.1 mm$^2$, often at least about 0.2 mm$^2$ and sometimes at least about 0.3 mm$^2$, where the total effective cross sectional area at the distal end of the first lumen may be as large as 0.6 mm$^2$ or larger, but in certain embodiments will not exceed about 0.5 mm$^2$ and in other embodiments will not exceed about 0.4 mm$^2$.

The second lumen of the subject catheter device is employed to convey or deliver a pH elevating fluid, e.g. a buffer, to a vascular site, as described in greater detail infra. As such, the second lumen of the subject multi-lumen catheter devices is characterized in that it is capable of being attached in fluid communication, either directly or indirectly, with a pH elevating fluid reservoir. The effective total cross-sectional area of the opening at the distal end of the second lumen, where effective total cross-sectional area is as defined above (e.g. the annular space in a coaxial embodiment, as described in greater detail infra), is sufficient to provide the requisite amount of pH elevating solution to the vascular site so that any portion of the vascular site apart from the target surface of the vascular solution is not contacted with a solution which has a pH of less than about 4, preferably less than about 5 and more preferably less than about 6. Accordingly, the effective cross-sectional area of the opening(s) of the distal end of the second lumen is at least about 0.8 mm$^2$, usually at least about 1.4 mm$^2$ and may be as larger as 2.2 mm$^2$ or larger, but generally does not exceed about 2.0 mm$^2$ and usually does not exceed about 1.5 mm$^2$.

The third lumen of the subject multi-lumen catheter devices is an aspiration lumen. The aspiration lumen is characterized, by at least having a distal opening(s) with an effective total cross-sectional area (e.g. the area of the annular space in the coaxial to embodiments described infra) that is sufficiently large to remove fluid, and debris, from the vascular site at substantially the same rate that fluid (e.g. buffer solution and acidic dissolution solution) is introduced into the vascular site during use of the device, such that the fluid pressure in the vascular site remains substantially isobaric or isometric, where by substantially isobaric or isometric is meant that the fluid pressure in the vascular site does not vary by more than about 50 mm Hg, preferably does not vary by more than about 10 mm Hg, and more preferably does not vary by more than about 5 mm Hg over the total flushing period.

The subject catheter devices are further characterized by at least including a first vascular occlusion means positioned at some point proximal to the distal end of the outer surface of the catheter device, e.g. the outer surface of the aspiration catheter in the coaxial embodiments described infra. By vascular occlusion means is meant any device or component that is capable of substantially, and preferably completely, occluding a vessel, e.g. an artery or vein. By substantially occluding is meant that fluid, e.g. blood, flow past the occlusion means upon activation is reduced by at least 95%, usually by at least 97% and more usually by at least 99%, where in preferred embodiments, fluid flow is reduced by 100% such that the fluid flow into the vascular site is substantially, if not completely, inhibited. Any convenient means may be employed, where a vascular occlusion means of particular interest includes an inflatable balloon. Inflatable balloons are well known in the catheter art, and any convenient balloon configuration may be employed. While the inflatable balloon may be one that is designed to be inflated with a gas or liquid, of particular interest in many embodiments are those that are configured to be inflated with a liquid, e.g. a pH elevating solution as described in greater detail infra.

Where this type of catheter or catheter system is provided in the subject kits, a number of distinct alternative embodiments of the subject catheter devices may be present in the kits. One preferred specific embodiment of interest is a coaxial embodiment, in which each of the first, second and third lumens are coaxial. Other alternative embodiments include embodiments in which at least one of the lumens is not coaxial with the other lumens, as well as embodiments in which none of the lumens is coaxial. Each of these representative alternative embodiments is now described in greater detail below.

As mentioned above, a preferred embodiment of the subject multi-lumen catheter devices is a coaxial embodiment, in which the first, second and third lumens of the subject catheter device are coaxial. By "coaxial" is meant that the first, second and third lumens share a common axis. As such, in these embodiments the first lumen is present in an element positioned inside the second lumen, which in turn is present in an element positioned inside the third lumen. Generally, the first, second and third lumens are found inside fluid delivery means which are positioned inside one another, where the fluid delivery means are often elongated tubular elements. The coaxially positioned fluid delivery means comprising the first, second and third lumens, i.e. the first, second and third fluid delivery means, may be held in a static relationship with respect to one or another or may be movable with respect to one another, such that at least one of the fluid delivery means, and preferably at least two of the fluid delivery means may be moved without moving the other fluid delivery means—i.e. each of the first, second and third fluid delivery means may be moved independently of one another. Spacers or other means on the inner walls of at least the second and third lumens may be present to maintain the coaxial configuration.

In this coaxial embodiment of the subject invention, one of the lumens serves to deliver an acidic dissolution fluid, one of the lumens serves to deliver a pH elevating fluid and one of the lumens serves to remove fluid from the vascular site. In other words, two of the lumens serve to introduce fluid to the vascular site and one of the lumens serves to remove fluid from the vascular site. While any of the lumens may serve any of the above functions, generally, the first lumen which delivers the acidic dissolution solution (i.e the one that has at least an inner surface that is substantially inert to the acidic dissolution fluid) is the innermost lumen of the coaxial lumens of the device. As such, the first lumen is the lumen with the inner walls that are closest to the center line or axis of the coaxial catheter device.

The first lumen is generally positioned along the center line or axis of a first elongated fluid delivery means, where the fluid delivery means generally extends along the length of the catheter from its proximal to distal end. The fluid delivery means is typically tubular in shape, and may have a variety of different cross-sectional configurations, including square, triangular, trapezoidal, circular, elliptical, irregular, and the like, where often the cross-sectional shape of the elongated tubular member is curvilinear, and more often is circular.

The design of the first fluid delivery means may vary depending on the nature of the target vascular occlusion e.g. whether the target vascular occlusion is a total occlusion or a partial occlusion. The total occlusion first fluid delivery means, e.g. the total occlusion catheter insert, is an elongated tubular structure, as described above, having a blunt ended, open distal end through which fluid may be flowed under pressure. The length of the total occlusion catheter insert generally ranges from about 90 to 210 cm, usually from about 100 to 190 cm and more usually from about 110 to 150 cm. The outer diameter of the total occlusion catheter insert is such that the catheter insert may be slidably positioned in the second lumen (i.e. the lumen of the second fluid delivery means, as described infra), and typically ranges from about 0.4 to 2.0, usually from about 0.4 to 1.6 mm. The inner diameter of the total occlusion catheter insert typically ranges from about 0.2 to 1.0, usually from about 0.25 to 1.0 and more usually from about 0.3 to 1.0 mm.

Where the target occlusion is a partial occlusion, a partial occlusion first fluid delivery means is employed, i.e. a partial occlusion catheter insert. The partial occlusion catheter insert differs from the total occlusion catheter insert in a number of ways. First, the partial occlusion catheter insert includes a balloon or analogous vessel occlusion means at its distal end, where the distance between the vascular occlusion means and the distal end of the catheter insert typically ranges from 1 to 30 mm, usually from about 10 to 20 mm. Second, the partial occlusion vascular insert has one or more fluid introduction ports proximal to the proximal side of the distal balloon. The diameter of the infusion ports may vary, but typically ranges from about 0.2 to 1.2, usually from about 0.4 to 1.0 and more usually from about 0.5 to 0.8 mm. Where the vascular occlusion means on the partial occlusion catheter insert is a balloon, a balloon inflation lumen is also present in the partial occlusion catheter insert. Finally, the end of the partial occlusion catheter insert is sealed. The length of the partial occlusion catheter insert generally ranges from about 90 to 250 cm, usually from about 100 to 230 cm and more usually from about 110 to 190 cm. The outer diameter of the partial occlusion catheter insert is such that the catheter insert may be slidably positioned in the second lumen, i.e. the lumen of the second fluid delivery means, as described infra. The outer diameter typically ranges from about 0.5 to 2.0. The inner diameter of the partial occlusion catheter insert typically ranges from about 0.2 to 1.0, usually from about 0.25 to 1.0 and more usually from about 0.3 to 1.0 mm.

The above described partial and total catheter inserts are further characterized by being capable of being attached at their proximal ends, either directly or through one or more attachment means, to a fluid reservoir, e.g. an acidic dissolution fluid reservoir and, in the case of the partial occlusion catheter insert, a balloon inflation means.

Figure 7A:
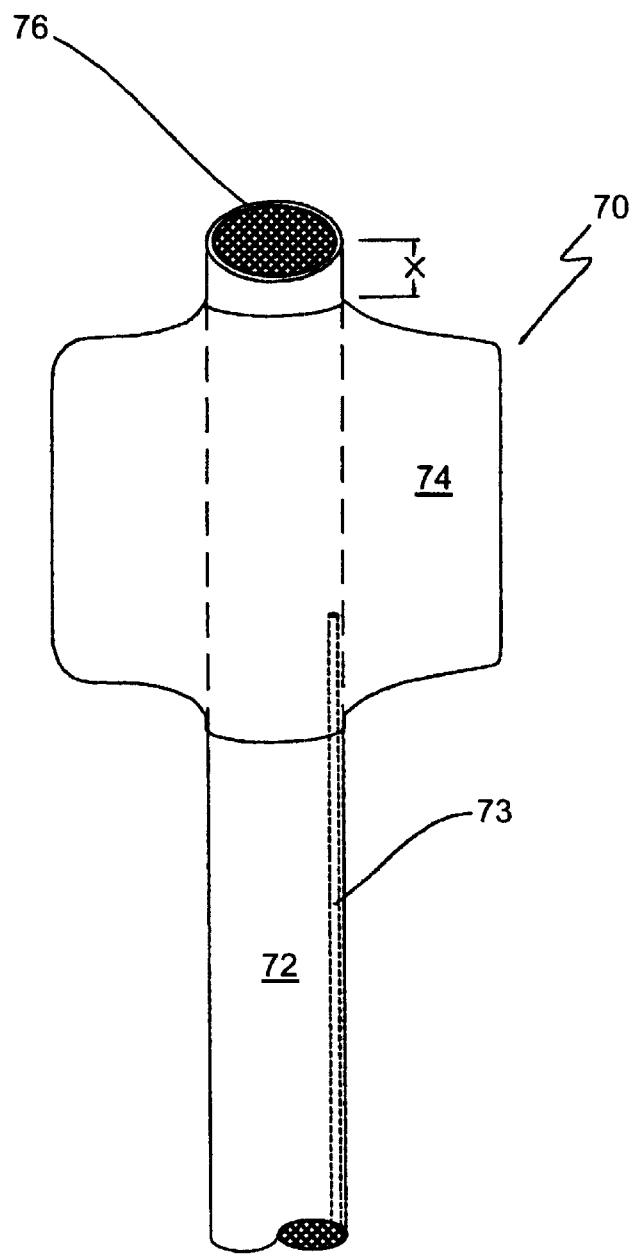
FIG. 7A provides a representation of an aspiration catheter according of an embodiment of the subject invention while FIG. 7B provides a representation of a total occlusion catheter insert for use in the aspiration catheter of FIG. 7A, where these catheters may be present in a kit according to the subject invention.
Figure 7B:
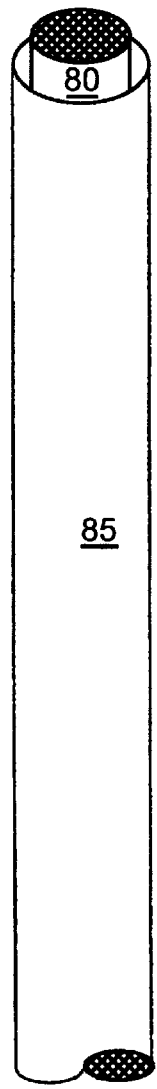
Figure 8:
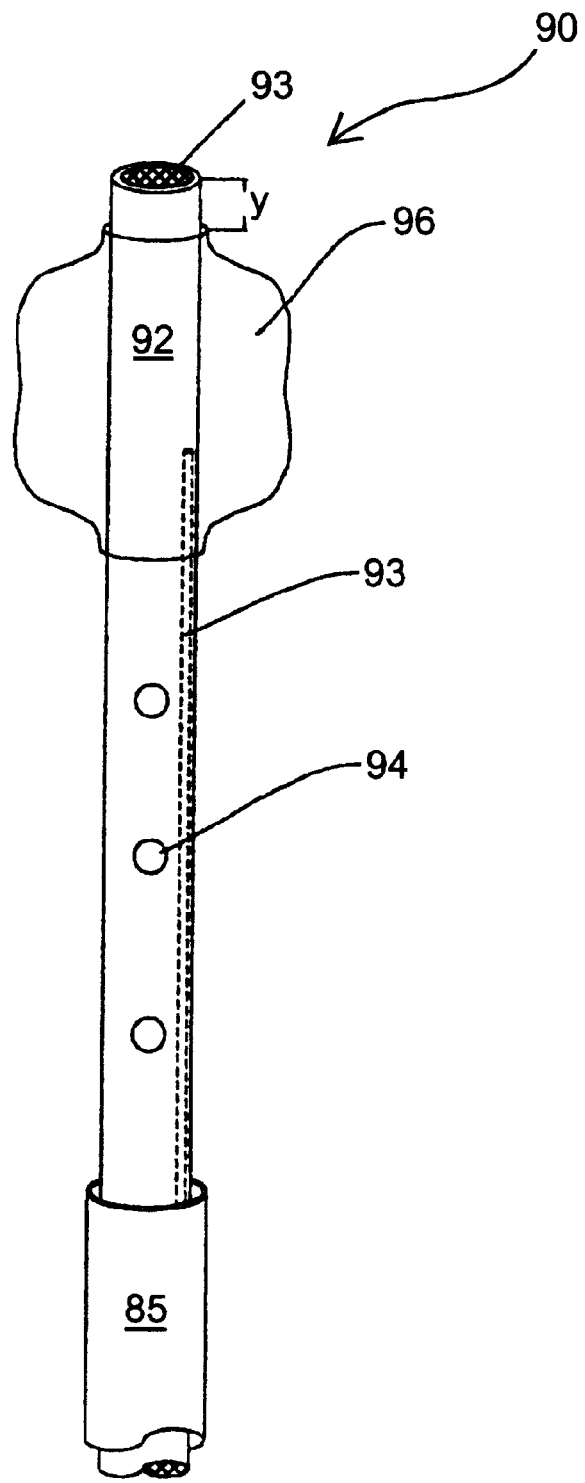
FIG. 8 provides a representation of a partial occlusion catheter insert for use in the aspiration catheter of FIG. 7A, which insert may also be present in kits according to the subject invention.

A representation of a total occlusion catheter insert 80 according to the subject invention is provided in FIG. 7B. A representative partial occlusion catheter insert is provided in FIG. 8. In FIG. 8, partial occlusion catheter insert 90 includes elongated tubular structure 92 that is sealed at its distal end 98. Proximal to the distal end 98 is balloon 96, where the distance Y typically ranges from about 1 to 30 mm, usually from about 10 to 20 mm. Also depicted are infusion ports 94. The diameter of the infusion ports may vary, but typically ranges from about 0.2 to 1.2, usually from about 0.4 to 1.0 and more usually from about 0.5 to 0.8 mm. Also shown is balloon inflation lumen 93, where the balloon inflation lumen has dimensions similar to those of balloon inflation lumen 73. As evidenced, the partial occlusion catheter insert includes two lumens, a fluid introduction lumen and a balloon inflation lumen. Also visible in FIGS. 7B and 8 is second delivery means 85 which includes the second lumen, described in greater detail below.

The second lumen of the subject multi-lumen catheter devices is designed for delivery of a pH elevating solution to the vascular site of the target occlusion. This lumen is generally present in a second fluid delivery means (element 85 in FIGS. 7B and 8), where the fluid delivery means is generally an elongated tubular structure analogous to the first fluid delivery means described supra. In the present coaxial embodiment, the dimensions of this second fluid delivery means, i.e. second catheter insert, are such that the first fluid delivery means or catheter insert described above (i.e. either the partial or total occlusion catheter insert) can fit inside this second fluid delivery means, i.e. can fit inside the lumen of the second fluid delivery means. A further limitation is that the first fluid delivery means must fit inside the second fluid delivery means in a manner such that an annular space is formed in the second lumen which is sufficient to convey the requisite amount of pH elevating fluid to the vascular site during use of the device. As such, the inner diameter of the second lumen exceeds the outer diameter of the first fluid delivery means by at least about 0.6 mm; sometimes at least about 0.9 mm and in certain embodiments at least about 1.2 mm. Accordingly, the inner diameter of the second fluid delivery means ranges from about 0.8 to 2.5, usually from about 0.9 to 1.9 and more usually from about 1.0 to 1.3 mm. The second fluid delivery means has an open distal end which, when positioned around the first fluid delivery means during use, forms an annular opening through which pH elevating fluid flows out of the second fluid delivery means and into the vascular site during use. The total effective cross-sectional area of the annular opening typically ranges from about 0.6 to 2.6, usually from about 0.8 to 1.9 and more usually from about 0.9 to 1.3 mm$^2$. The overall length of the second fluid delivery means typically ranges from about 90 to 210, usually from about 100 to 190 and more usually from about 110 to 150 cm. The second fluid delivery means is further characterized by having a means for connecting to a pH elevating fluid reservoir, either directly or indirectly, at its proximal end.

The first and second lumens and their respective fluid delivery means may be combined into integrated catheters in certain embodiments. An example of a total occlusion catheter unit is presented in FIG. 11 while an example of a partial occlusion catheter un it is presented in FIG. 12.

The third lumen in this coaxial embodiment of the subject devices is the outermost lumen, which is generally present in an elongated tubular structure analogous to the first and second fluid delivery means, as described above. The third lumen present in this third fluid delivery means is employed to remove fluid from the vascular site. As such, this third fluid delivery means is properly viewed as an aspiration catheter. The aspiration catheter is generally an elongated tubular structure fabricated from a flexible, biologically acceptable material having a balloon or analogous vessel occlusion means positioned at its distal end. The length of the aspiration catheter may vary, but is generally from about 80 to 200 cm, usually from about 90 to 180 cm and more usually from about 100 to 140 cm. The outer diameter of the aspiration catheter is selected so as to provide for access of the distal end of the catheter to the vascular site via the vascular system from the remote point of entry, where the outer diameter typically ranges from about 1.0 to 4.0 mm (3 to 12 Fr), usually from about 1.5 to 3.0 mm (4.5 to 9.0 Fr) and more usually from about 1.7 to 2.7 mm (5 to 8 Fr). The aspiration catheter is characterized by having an open distal end, where the inner diameter at the open distal end is sufficient to house the first and second coaxial fluid delivery means, as described supra, and remove fluid from the vascular site at the desired rate, e.g. a rate that provides for substantially isometric or isobaric pressure in the vascular site during treatment, through the resultant annular space. The inner diameter of the third or aspiration lumen, at least at its distal end and generally along the entire length of the aspiration catheter, typically ranges from about 0.2 to 2.0, usually from about 0.25 to 1.75 and more usually from about 0.35 to 1.5 mm. The total effective cross-sectional area at its distal end, i.e. the cross-sectional area of the annular space at the distal end opening, typically ranges from about 1.3 to 3.9, usually from about 1.3 to 3.2 and more usually from about 1.3 to 2.5 mm$^2$. Also present at the distal end of the aspiration catheter is a vessel occlusion means, where the vessel occlusion means is usually an inflatable balloon. The balloon is one that is inflatable to a volume sufficient to substantially occlude the vessel in which the aspiration catheter is positioned, e.g. by pressing against the intimal surface of the vessel in which the aspiration catheter is positioned. The balloon is in fluid or gaseous communication with an inflation lumen that runs the length of the aspiration catheter and can be connected to a balloon inflation means. The inflation lumen has an.inner diameter that typically ranges from about 0.1 to 0.5, usually from about 0.2.to 0.4 mm. In certain embodiments, the aspiration catheter further includes a separate guidewire lumen. When present, the guidewire lumen has a diameter ranging from about 0.2 to 1.0 mm, usually from about 0.3 to 0.6 mm. Thus, the aspiration catheter includes at least two distinct lumens, i.e. an aspiration lumen (also referred to herein as the third lumen) and a balloon inflation lumen, and in many embodiments includes three distinct lumens, i.e. an aspiration lumen, a balloon inflation lumen and a guidewire lumen. A representation of an aspiration or irrigation catheter is provided in FIG. 13.

The aspiration catheter is further characterized by being capable of attaching, either directly or through one or more attachment means, at its proximal end to vacuum means, e.g. a negative pressure means, where such means is sufficient to provide for the desired aspiration during use of the device, and a balloon inflation means, where such means is sufficient to inflate the balloon at the distal end of the catheter when desired.

A representation of the aspiration catheter of the subject catheter systems found in the subject kits is provided in FIG. 7A. In FIG. 7A, aspiration catheter 70 includes elongated tubular member 72 and balloon 74 located proximal to the distal end. The distance X between the distal most portion of the balloon 74 and the distal end of the catheter typically ranges from about 1 to 20, usually from about 5 to 10 mm. Also shown is distal open end 86 through which either the partial or total occlusion insert catheter is moved and fluid is aspirated. Balloon 84 is inflatable via balloon inflation lumen 83.

In an alternative embodiments of the subject invention, at least two of the first, second and third lumens are not coaxial. In these alternative embodiments, the configuration of the first, second and third lumens in the device may vary greatly. For example, the first second and/or third lumens may be present on separate non-coaxial fluid delivery means. As such, the device could be made up of three different fluid delivery means bundled together to produce a triple lumen catheter device. Alternatively, a single fluid delivery means could house all three lumens. In certain embodiments, two of the lumens, i.e. the first and second lumen, will be present on a first fluid delivery means, which fluid delivery means is coaxially positioned within the third lumen. The first or internal fluid delivery means housing the first and second lumens may take on a variety of configurations. In one configuration, the first and second lumens terminate or open at the distal end of the internal fluid delivery means. In other configurations, one of the lumens opens at a different area from the other lumen. In these embodiments, the first lumen typically opens at the distal end of the internal fluid delivery means and the second lumen opens at a site proximal to the distal end of the internal fluid delivery means. The second lumen may open up at a one or more openings proximal to the distal end of the internal fluid delivery means. In each of these embodiments, the internal fluid delivery means housing the first and second lumens is present in a third lumen which is also housed by a fluid delivery means, where this fluid delivery means may be referred to as an aspiration catheter, as described above.

As mentioned above, the above described catheter devices may be present in the subject kits as catheter systems. By catheter system is meant two more disparate catheter components which are capable of being assembled into a single unit, i.e. coaxial catheter assembly, having at least an inner catheter that is slidably positioned within the lumen of an outer catheter, i.e. a coaxial catheter assembly having an inner insert catheter that can be moved relative to the outer catheter so as to produce varying distances between the distal ends of the two coaxial catheters. For example, a catheter system which includes the above described coaxial embodiments where all three first, second and third lumens are coaxial, will include disparate catheter fluid delivery means that fit within one another to produce a coaxial triple lumen catheter as described above. In such systems, the system will at least include an aspiration catheter, a pH elevating fluid delivery catheter and at least one internal fluid delivery catheter. In many systems according to this embodiment, the system will further include a second internal catheter, such that the first internal catheter is suitable for use in treating total occlusions and the second internal catheter is suitable for use in treating partial occlusions.

Figure 9:
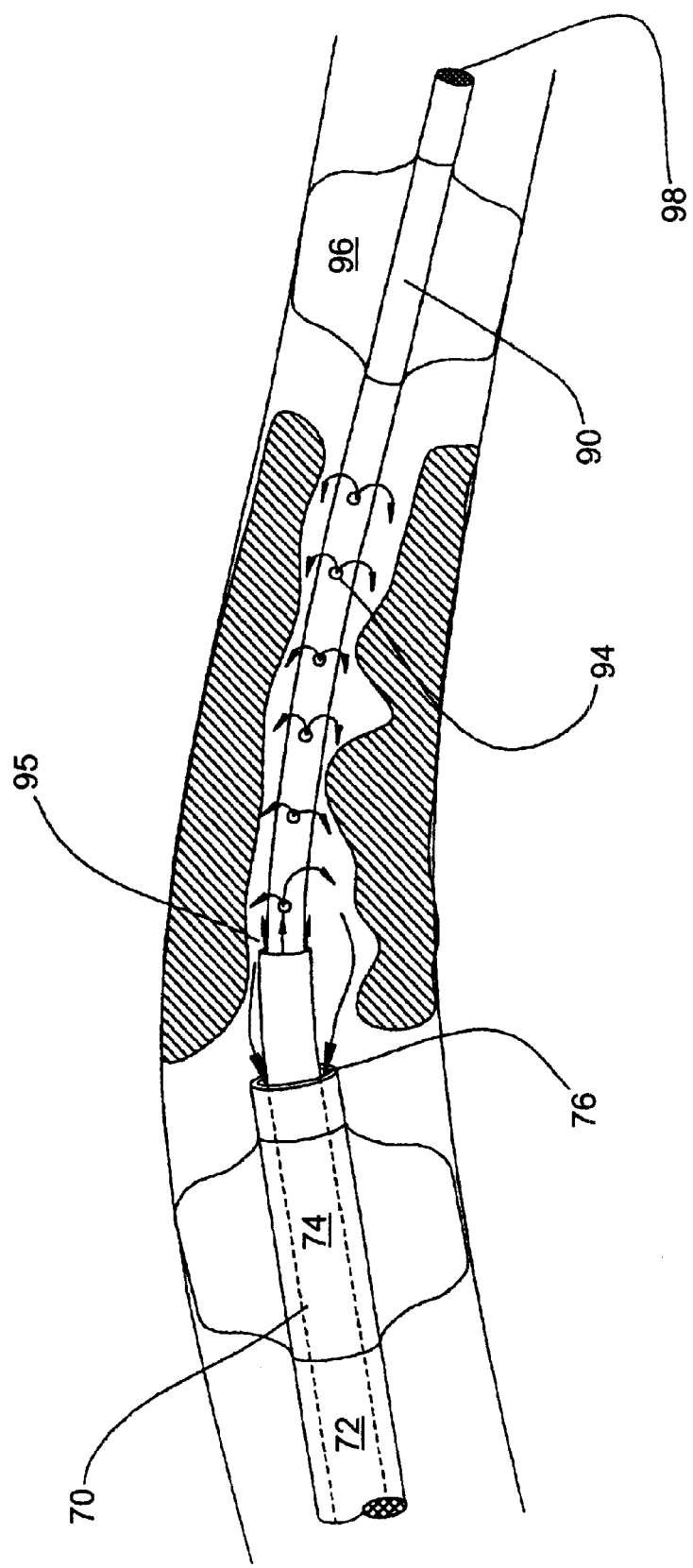
FIG. 9 provides a depiction of the use of the partial occlusion catheter system which can be fabricated from catheter components found in kits according to the subject invention.
Figure 10:
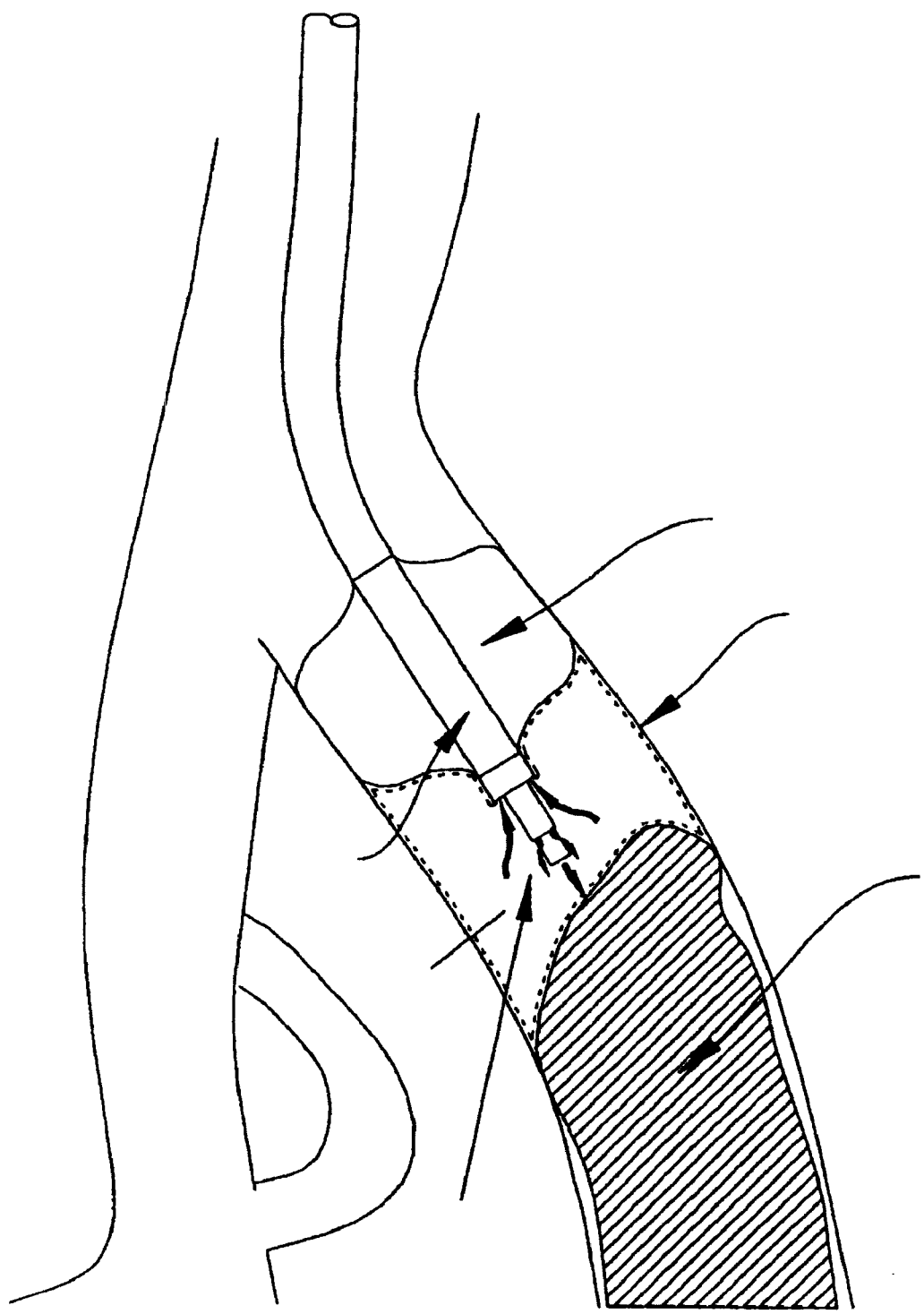
FIG. 10 provides a depiction of the use of a total occlusion catheter system which can be fabricated from catheter components found in kits according to the subject invention.
Figure 11:
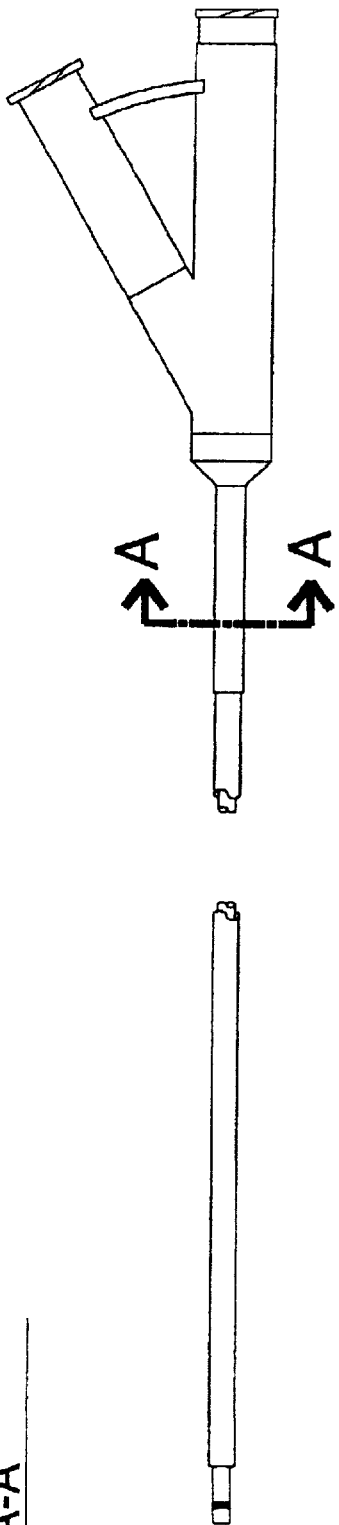
FIG. 11 provides another view of a total occlusion catheter of the catheter systems that may be found in kits of the subject invention.
Figure 11:
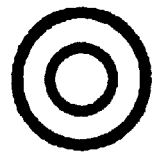
Figure 12:
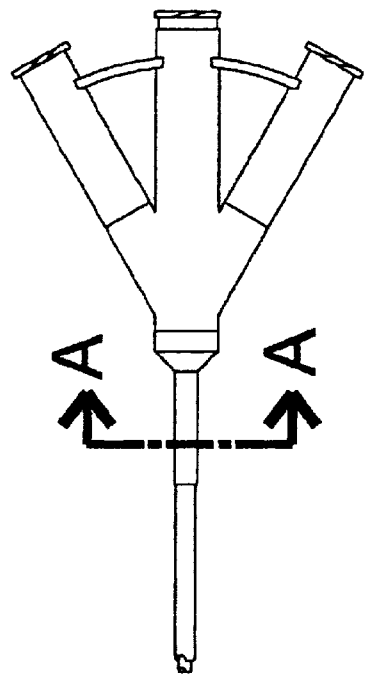
FIG. 12 provides another view of a partial occlusion catheter of the catheter systems that may be found in kits of the subject invention.
Figure 12:
Figure 12:
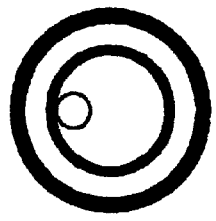

An exemplary catheter system of the subject invention includes the partial occlusion catheter unit, the total occlusion catheter unit and the irrigation or aspiration catheter unit depicted in FIGS. 11 to 13. FIGS. 9 and 10 provide a representation of how these system components fit together and operated when used. In. FIG. 9, a coaxial partial occlusion catheter device, as described above, is shown introduce both acidic dissolution fluid and pH elevating fluid into a target vascular site that houses a partial occlusion. In FIG. 9, the catheter device is introduced into the vascular site such that the balloon 96 of the partial occlusion insert 90 and the balloon 74 of the aspiration catheter 70 flank the partial occlusion. Acidic dissolution fluid is introduced by the plurality of ports 94 on the partial occlusion insert. A pH elevating solution is concomitantly introduced through annular space 95. Fluid is then removed from the vascular site by the aspiration catheter 70 through annular space 76. FIG. 10 provides a view of a total occlusion catheter insert flushing a vascular site of a total occlusion. As can be seen in FIG. 10, acidic dissolution fluid is introduced through.the central catheter and pH elevating solution is introduce via the catheter immediately concentric with the center catheter. Fluid is removed from the vascular site via the aspiration catheter, in which the central and intermediate catheters are coaxially positioned.

Instructions for Use

In addition to at least one of (a) the dissolution fluid and (b) the fluid introduction means, as described above, the subject kits also include instructions for using the components of the kit to treat a vascular calcified lesion. Specifically, the subject kits also include instructions for using the components of the kit in methods of treating vascular calcified lesions, such as total and partial calcified vascular occlusions, etc. Methods of using a fluid introduction means and a dissolution fluid to treat vascular calcified lesions are described in U.S. patent application Ser. Nos. 09/425,826; 09/384,860; 09/353,127; 09/195,291 and 09/118,193; the disclosures of which applications are herein incorporated by reference.

The instructions present in the subject kits generally describe a method for at least reducing the mineral content of a vascular calcified lesion by contacting the lesion with a fluid capable of locally increasing the proton concentration in the region of the lesion. As used herein, the term "vascular" is used broadly to refer to the circulatory system of an organism. As such, the term "vascular" refers to arteries and veins, as well as specialized organs that are closely associated with the circulatory system, such as the heart. The term "cardiovascular" refers to that portion of the vascular system that is closely associated with the heart. Thus, target lesions of the methods described in the instructions of the subject kits are vascular calcified lesions, including cardiovascular calcified lesions.

A lesion is considered to be a vascular calcified lesion if it is present on a vascular structure. Vascular structures include vascular tissues as well as vascular implants positioned within the vascular system. Vascular tissue refers to any tissue that is present in the circulatory system of the host, as described above, and as such includes not only vessel tissue, such as arterial and venous tissue, but also cardiac or heart tissue including valves and other cardiovascular features or specialized tissue structures. Vascular implants include prosthetics that have been introduced into the vascular system, including bioprosthetics, etc, such as allogeneic and xenogeneic implants, e.g. heart valves, synthetic implants, vascular replacements or grafts, e.g. saphenous vein grafts, artificial hearts, left ventricular assist devices, electrodes, and the like. Thus, vascular structures include both naturally occurring vascular tissue and implants of exogenous origin that have been introduced into the circulatory system.

The vascular structure on which the target calcified lesion is present is a structure found on the blood side of the circulatory system, by which is meant that the structure is found on the side of the circulatory system adjacent to blood flow and which comes into contact with blood, and not on the outside of the circulatory system, i.e. that portion of the circulatory system that does not contact blood. As such, the lesion may be present on: (a) the inner wall or intima of a blood vessel; (b) a valve present in a blood vessel; (c) a heart valve; (d) an implant present in an artery or vein; etc.

The calcified target lesion may be a substantially pure mineral deposit or coating over the surface of a region of vascular tissue, such as a coating or layer on at least a portion of valve tissue and the like, or may be a more complex formation that includes both mineral and other components, including organic matter, e.g. lipids, proteins, and the like.

The mineral component making up the calcified lesion is generally made up of one or more calcium phosphates, where the calcium phosphates are generally apatitic. The term "apatite" as used herein refers to a group of phosphate minerals that includes ten mineral species and has the general formula $X_5(YO_4)_3Z$, where X is usually $Ca^{2+}$ or $Pb^{3+}$, Y is $P^{5+}$ or $As^{5+}$, and Z is $F^-$, $Cl^-$, or $OH^-$. The term calcium apatite refers to a group of phosphate minerals where X is $Ca^{2+}$. The mineral component of the calcified lesion typically includes one or more of hydroxyapatite, carbonated hydroxyapatite (dahllite) and calcium deficient hydroxyapatite.

In addition to the mineral component, the lesion that is the target of the subject methods may also comprise one or more additional components, where such components include: lipids; lipoproteins; proteins; including fibrinogen, collagen, elastin and the like; proteoglycans, such as chondroitin sulfate, heparin sulfate, dermatans, etc. and cells, including smooth muscle cells, epithelial cells, macrophages and lymphocytes. As such, calcified lesions that are targets of the subject methods include: type IV, type V and type VI lesions, as defined in Stary et al., Arterioscler Thromb Vasc Biol. (1995)15:1512–1531.

In arterial lesions that are targets of the subject methods, the mineral component of the calcified lesion generally makes up from about 10 to 100, usually from about 10 to 90 and more usually from about 10 to 85 dry weight % of the lesion. The size of the lesion, that is the target of the subject methods varies depending on whether it is a lesion found in arteries, in the aorta or on a valve, e.g. a heart valve. As such, the size of the lesion may vary substantially, but will typically cover an area, e.g. surface of arterial intima, of at least about 1 $mm^2$, usually at least about 4 $mm^2$ and more usually at least about 10 $mm^2$, where the area covered by the lesion may be as 40 $mm^2$ or larger, but will usually not exceed about 20 $mm^2$, and more usually will not exceed about 15 $mm^2$.

In the methods described in the instructions present in the subject kits, the mineral content of vascular calcified target lesions (as described above) is reduced according to the subject invention by maintaining the local environment of the lesion at a subphysiological pH for a sufficient period of time for the desired amount of demineralization to occur. By local environment of the lesion is meant the immediate vicinity of the lesion, such as the area defined by a set distance from any surface point (i.e. point not adjacent or juxtaposed to the vesicular tissue, e.g. intima, with which the lesion is associated) on the lesion, typically extending at least 1 $mm^2$, usually at least 2 $mm^2$ beyond the area covered by the lesion, and in many embodiments substantially further beyond the area covered by the lesion. For example, where the target lesion covers a 4 $mm^2$ surface of arterial intima, the local environment will extend to cover an area of 6 $mm^2$. In three-dimensional terms, where a lesion occupies a volume of 8 $mm^3$, the volume of the local environment will be at least 9 $mm^3$ and will often be larger. In many embodiments, the local environment may extend beyond this limited area. For example, the local environment may be a mechanically isolated section of a vessel or valve in which the lesions are present, where the volume of such an isolated section may range from about 4 to 4000 $mm^3$, usually from about 40 to 2000 $mm^3$ and more usually from about 100 to 1000 $mm^3$. Furthermore, the local environment may be an isolated limb or portion thereof. In yet other embodiments, the local environment may be a given length of a blood vessel, e.g. an artery, that has been cannulated on either side of the lesion (e.g. in those embodiments where the target lesion is a diffuse lesion that extends for a given length of the blood vessel). In certain embodiments, the volume of the local environment of the lesion ranges from about 1 to 100, usually from about 5 to 50 and more usually from about 10 to 20 fold greater than the volume of the lesson, where the local environment volume includes the volume of the lesion. In other embodiments, the local environment includes a defined area adjacent to only one side of the target lesion, e.g. where the target lesion is a substantially complete vascular occlusion. In such embodiments, the local environment will not necessarily be larger that the total volume of the target lesion, but will instead merely include the region of the vessel volume adjacent to one surface of the vascular occlusion. Importantly, however, the local region does not include the entire vascular system. As such, the local environment of lesion is less than 90%, usually less than 80% and more usually less than 50% of the entire volume (e.g. the volume of circulating blood) of the vascular system of the host or subject being treated. In many embodiments, the local environment is less than 5% and typically between about 1 to 2% of the entire volume of the vascular system of the host.

Preferably, the local environment of the lesion is at least substantially bloodless, by which is meant that the local environment contains substantially no blood components, particularly red blood cells, white blood cells, platelets, serum proteins, e.g. albumin, and the like. By substantially bloodless is meant that the local environment includes less than 75%, usually less than 50% and more usually less than 25% of the blood components originally present in the local environment (where percentage is based on dry weight), where the number of originally present blood components in the local environment is preferably less than 20%, more preferably less than 15% and most preferably less than 10%. The local environment is rendered substantially bloodless using any convenient methodology, where representative methodologies include the inflation of occlusion balloons on either side of the target lesion, etc.

As mentioned above, the pH in the local environment is maintained at a subphysiological level for a sufficient period of time for the desired amount of demineralization of the target lesion to occur. Typically, the pH is maintained at a value that does not exceed about 5 and usually does not exceed about 4, and more usually does not exceed about 3. In many embodiments, the pH of the dissolution solution ranges from between 0 and 1. Within the above range, the pH may be constant or variable over the course of the demineralization procedure, i.e. over the period of time during which the pH of the local environment is maintained at a subphysiological value.

The time period during which the local pH is maintained at a subphysiological level in the local region of the lesion is sufficient for the desired amount of demineralization to occur. As such, the pH of the local environment is maintained at a subphysiological value for a period of time ranging from about 5 to 200 minutes, usually from about 10 to 100 minutes and more usually from about 10 to 30 minutes.

The pH of the local environment in the region of the lesion may be maintained at the requisite subphysiological level using any convenient protocol. Where a substantially constant subphysiological level is desired, a dynamic introduction of the fluid into the local environment is employed. Alternatively, where some variability in the pH of the local environment is acceptable, a static introduction of the fluid into the local environment may be employed.

By static is meant that a predetermined amount of dissolution solution is introduced into the local environment of the lesion and maintained in the local environment of the lesion for the entire treatment period, without the addition of further quantities of dissolution solution. By dynamic is meant that the dissolution solution is introduced into the local environment of the lesion one or more times, including continuously, during the treatment period. As mentioned above, the local environment of the lesion has preferably been rendered bloodless prior to introduction of the dissolution fluid.

During the dissolution procedure, protons from the local environment are removed as a result of the demineralization process. As such, it is often desirable to introduce the dissolution solution into the local environment of the lesion in a dynamic manner. Dynamic introduction of the dissolution solution typically involves flushing the lesion with the dissolution solution, where flushing involves a continuous flow of the dissolution solution across at least a surface of the lesion, where the flow may be under pressure (e.g. where the fluid is emitted from the delivery device under enhanced pressure, as described in greater detail infra). In other words, the dissolution fluid is continuously flowed through the local environment of the lesion for the period of time required for the desired amount of demineralization to occur. Simultaneously, fluid is removed from the local environment of the lesion such that the overall volume of fluid in the local environment of the lesion remains substantially constant, where any difference in volume at any two given times during the treatment period does not exceed about 50%, and usually does not exceed about 10%. In this manner, the pressure of the localized environment of the lesion is maintained at a substantially constant value, thereby minimizing traumatic impact on the vessel walls in the region of the lesion.

Where the lesion is flushed with the dissolution solution, the flow rate of the dissolution solution through the local environment of the lesion is generally at least about 1 volume/minute, usually at least about 2 volumes/minute and more usually at least about 10 volumes/minute, where the flow rate may be as great as 100 volumes/minute or greater, but usually does not exceed about 1000 volumes/minute and more usually does not exceed about 500 volumes/minute, where by "volume" is meant the volume of the local environment of the lesion.

When treatment involves dynamic flushing of the local environment of the lesion, the total amount of dissolution fluid that is passed through the local environment of the lesion during the treatment period typically ranges from about 0.01 to 50 liters, usually from about 0.1 to 5.0 liters and more usually from about 0.1 to 2.0 liters. In contrast, where a static methodology is employed, the total amount of dissolution fluid that is introduced into the local environment of the lesion ranges from about 10 ml to 1 liter, and usually from about 10 to 500 ml.

Maintenance of the local environment of the calcified lesion at a subphysiologic pH, as described above, results in at least partial demineralization of the lesion, i.e. at least a reduction of the calcium phosphate content of the lesion. By reduction is meant that the total overall dry weight of calcium phosphate mineral is reduced or decreased, generally by at least about 50%, usually by at least about 75% and more usually by at least about 90%. In certain embodiments, substantially all of the calcium phosphate content of the lesion may be removed, where by substantially all is meant at least about 90%, usually at least about 95% and preferably at least about 99% dry weight of the original calcium phosphate present in the lesion is removed.

The instructions for practicing the above described methods or variations thereof, e.g. variations which include the administration of a pH elevating fluid as described in U.S. patent application Ser. No. 09/425,826, the disclosure of which is herein incorporated by reference, etc., are generally recorded on a suitable recording medium. For example, the instructions may be printed on a substrate, such as paper or plastic, etc. As such, the instructions may be present in the kits as a package insert, in the labeling of the container of the kit or components thereof (i.e. associated with the packaging or subpackaging) etc. In other embodiments, the instructions are present as an electronic storage data file present on a suitable computer readable storage medium, e.g. CD-ROM, diskette, etc.

Requisite Kit Components Summary

As summarized throughout the above description, the subject kits at least include one of (a) a fluid delivery means and (b) a dissolution fluid (or component(s) thereof) and, in many embodiments, instructions for using the kit components to treat a vascular calcified lesion, where each of these elements is described above. As such, certain embodiments of the subject kits include a fluid delivery means and instructions for using the fluid delivery means with a dissolution fluid to treat a vascular calcified lesion. Conversely, other embodiments of the subject kits include a dissolution fluid and instructions for using the dissolution fluid with a fluid delivery means to treat a vascular calcified lesion. In yet other embodiments, the kits may contain the dissolution fluid and the fluid delivery means, but not the instructions. In still yet other embodiments, the subject kits include both a fluid delivery means and a dissolution fluid, in conjunction with instructions for using the components to treat a vascular calcified occlusion. A representation of a kit representative of this embodiment is shown in FIG. 14. In the kit represented in FIG. 14, a tray 140 is present that includes three different catheter components of a catheter fluid delivery system, i.e. aspiration catheter 142, partial occlusion catheter insert 144 and total occlusion catheter insert 146. Also present in the kit is a bottle 148 containing the dissolution fluid.

Optional Kit Components

The kits of the subject invention may also include a number of different optional components, which may find use in certain variations of the above described basic methods of treating calcified vascular lesions. One such optional component that may be present in the subject kits is a pH elevating solution. By pH elevating solution is meant any solution that, upon combination with the acidic dissolution solution, produces a solution with an elevated pH with respect to the acidic dissolution solution. In principle, any fluid that, upon combination of with the acid dissolution fluid produces a solution having a pH higher than that of the acidic dissolution fluid, may be employed, so long as the fluid is biocompatible, at least for the period of time that it is present in the target vascular site. The pH elevating solution should have a pH of at least about 4, usually at least about 6 and more usually at least about 8. As such, pH elevating fluids of interest include water, physiological acceptable buffer solutions, etc., where in many embodiments, the pH elevating solution is a buffer solution. Representative buffer solutions of interest include: phosphate buffered saline, sodium bicarbonate and the like. In certain embodiments, the kits may include one or more precursor components of the pH elevating fluid, e.g. dried reagents that can be combined with water at the time of use to produce the pH elevating fluid.

Another optional component that may be present in the subject kits is a guidewire. Any convenient type of guidewire may be present, where a number of different guidewires are known to those of skill in the art. Guidewires of interest include those described in U.S. Pat. Nos. 6,007,514; 5,980,471; 5,957,865; 5,938,609; 5,931,819; 5,916,178; 5,908,395; 5,902,254; 5,865,767; 5,827,201; 5,788,654; 5,772,609; 5,769,796; 5,755,695; 5,749,837; 5,682,897; 5,660,180; 5,636,642; 5,606,981; 5,599,492; 5,596,996; 5,558,093; 5,546,948; 5,520,189; 5,507,301; 5,497,782; D363,776; 5,460,187; 5,441,497; 5,437,288; 5,427, 118; 5,421,349; 5,411,033; 5,409,015; 5,368,035; 5,341, 818; 5,339,833; 5,313,967; 5,303,714; RE34,466; 5,265, 622; 5,238,005; 5,184,621; 5,167,239; 5,147,317; 5,144, 959; 5,111,829; 5,107,852; 5,095,915; 5,095,911 5,084,022; 5,069,226; 5,063,935; 4,966,163; 4,953,553; 4,875,489; 4,827,941; 4,811,743; 4,676,249; 4,534,363; 4,080,706; 4,003,369; the disclosures of which are herein incorporated by reference.

Additional optional components that may be present in kits of the subject invention include various fluids and solutions in addition to the dissolution fluid and pH elevating fluid described above. Additional fluids that may be present include: organic matter dissolution fluids, wash or rinsing fluids, imaging agent fluid mediums that include an imaging agent, such as a non-ionic imaging agents, e.g. CONRAY™, OXILAN™, fluids containing one or more pharmacological agents, e.g. agents that promote healing, reduce inflammation, and the like; etc.

Other components that may be present in the subject kits include one or more additional components and accessories for use with the fluid delivery means present in the kit, including tubing for connecting the various catheter components with fluid reservoirs, syringes, pumping means, etc., connectors, dilators, vacuum regulators, etc. Other elements that may be present in the subject kits Include various components of the systems, including manifolds, balloon inflation means, e.g. syringes, pumping means, negative pressure means etc.

It is evident from the above discussion that the subject kits conveniently provide one or more components necessary for efficiently treating vascular calcified lesions in a convenient and usable format. As such, the subject kits represent a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A kit for use in the treatment of vascular calcified lesions, said kit comprising:
    (a) at least one of:
        (i) an acidic dissolution fluid having a pH of less than about 3.0 or a component(s) thereof; and
        (ii) a localized fluid delivery means capable of conveying fluid to a vascular site; and
    (b) a recording medium having recorded thereon instructions for using said fluid delivery means and acidic dissolution fluid to treat a vascular calcified lesion.

2. The kit according to claim 1, wherein said fluid delivery means is capable of flushing said vascular site with said dissolution fluid.

3. The kit according to claim 1, wherein said fluid delivery means comprises at least one catheter.

4. The kit according to claim 2, wherein said fluid delivery means comprises at least two catheters capable of assuming a coaxial configuration.

5. The kit according to claim 1, wherein said acidic dissolution fluid is a hydrochloric acid solution.

6. The kit according to claim 1, wherein said kit comprises both of said fluid delivery means and said dissolution fluid or components thereof.

7. The kit according to claim 1, wherein said instructions are printed onto a substrate.

8. The kit according to claim 1, wherein said kit further comprises a buffer solution or a component(s) thereof.

9. A kit for use in the treatment of vascular calcified lesions, said kit comprising:
    (a) an acidic dissolution fluid having a pH of less than about 3.0;
    (b) a catheter fluid delivery system capable of localized flushing a vascular site with said dissolution fluid; and
    (c) instructions for using said fluid delivery means and dissolution fluid to treat a vascular calcified lesion, wherein said instructions are printed onto a substrate.

10. The kit according to claim 9, wherein said catheter fluid delivery system comprises at least two catheters capable of assuming a coaxial configuration.

11. The kit according to claim 9, wherein said catheter fluid delivery system comprises at least three catheters, at least two of which are capable of assuming a coaxial configuration.

12. The kit according to claim 9, wherein said acidic dissolution fluid is a hydrochloric acid solution.

13. The kit according to claim 12, wherein said hydrochloric acid solution comprises a salt.

14. The kit according to claim 13, wherein said salt is NaCl.

15. The kit according to claim 9, wherein said kit further comprises a guidewire.

16. The kit according to claim 9, wherein said kit further comprises a buffer solution.

17. A kit for use in the treatment of vascular calcified lesions, said kit comprising:
    (a) a hydrochloric acid dissolution solution having a pH ranging of less than about 3.0; and
    (b) a catheter fluid delivery system capable of localized flushing a vascular site with said hydrochloric acid dissolution solution, wherein said catheter fluid delivery system comprises at least two catheters capable of assuming a coaxial configuration.

18. The kit according to claim 17, wherein said kit further comprises instructions for using said fluid delivery means and dissolution fluid to treat a vascular calcified lesion, wherein said instructions are printed onto a substrate.

19. The kit according to claim 17, wherein said catheter fluid delivery system comprises at least three catheters, two of which are capable of assuming a coaxial configuration.

20. The kit according to claim 17, wherein said hydrochloric acid solution comprises a salt.

21. The kit according to claim 20, wherein said salt is NaCl.

22. The kit according to claim 17, wherein said kit further comprises a guidewire.

23. The kit according to claim 17, wherein said kit further comprises a buffer solution.

* * * * *